(12) United States Patent
Thanos et al.

(10) Patent No.: US 12,377,252 B2
(45) Date of Patent: Aug. 5, 2025

(54) IMPLANTATION DEVICES, SYSTEM, AND METHODS

(71) Applicant: Vertex Pharmaceuticals Incorporated, Boston, MA (US)

(72) Inventors: Christopher Thanos, Cumberland, RI (US); Moses Goddard, Boston, MA (US); Moses Sandrof, Boston, MA (US); John Mills, Warwick, RI (US); Megan Billings, Warwick, RI (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 1075 days.

(21) Appl. No.: 16/980,031

(22) PCT Filed: Mar. 12, 2019

(86) PCT No.: PCT/US2019/021904
§ 371 (c)(1),
(2) Date: Sep. 11, 2020

(87) PCT Pub. No.: WO2019/178134
PCT Pub. Date: Sep. 19, 2019

(65) Prior Publication Data
US 2021/0016073 A1 Jan. 21, 2021

Related U.S. Application Data

(60) Provisional application No. 62/642,529, filed on Mar. 13, 2018.

(51) Int. Cl.
*A61M 37/00* (2006.01)
*A61M 31/00* (2006.01)

(52) U.S. Cl.
CPC ...... *A61M 37/0069* (2013.01); *A61M 31/002* (2013.01); *A61M 2202/09* (2013.01); *A61M 2205/586* (2013.01)

(58) Field of Classification Search
CPC .................................. A61M 37/0069
See application file for complete search history.

(56) References Cited

U.S. PATENT DOCUMENTS

| 4,451,253 A | 5/1984 | Harman |
| 5,814,020 A | 9/1998 | Gross |

(Continued)

FOREIGN PATENT DOCUMENTS

| CN | 1238706 A | 12/1999 |
| GB | 2470575 A | 12/2010 |

(Continued)

OTHER PUBLICATIONS

Extended European Search Report, mailed Nov. 9, 2021 for Application No. EP 19767143.

(Continued)

*Primary Examiner* — Dung T Ulsh
(74) *Attorney, Agent, or Firm* — Wolf, Greenfield & Sacks, P.C.

(57) ABSTRACT

Provided herein are devices, systems, and methods for subcutaneous membrane, encapsulation chamber, or reservoir implantation comprising or employing an implantation device configured to insert a membrane, encapsulation chamber, or reservoir into a subject.

45 Claims, 15 Drawing Sheets

(56) References Cited

U.S. PATENT DOCUMENTS

| | | | |
|---|---|---|---|
| 2007/0156103 A1 | 7/2007 | Chatlynne et al. | |
| 2010/0286613 A1 | 11/2010 | Ring | |
| 2011/0224648 A1 | 9/2011 | Secci | |
| 2014/0323907 A1* | 10/2014 | Frazier | A61M 5/00 604/93.01 |
| 2015/0297294 A1 | 10/2015 | So et al. | |
| 2016/0243026 A1* | 8/2016 | Pathak | A61K 31/496 |
| 2016/0296739 A1* | 10/2016 | Cleveland | A61M 5/31526 |
| 2017/0065805 A1* | 3/2017 | Tutera | A61M 37/0069 |
| 2018/0263238 A1 | 9/2018 | Flanagan et al. | |
| 2019/0201329 A1* | 7/2019 | Lee | A61M 37/0069 |
| 2019/0255308 A1* | 8/2019 | Virden | A61M 37/0069 |

FOREIGN PATENT DOCUMENTS

| | | | | |
|---|---|---|---|---|
| JP | 60-129057 | A | 7/1985 | |
| JP | 50-51492 | U | 10/1997 | |
| JP | 2004-533275 | A | 11/2004 | |
| JP | 2009-544393 | A | 12/2009 | |
| JP | 2003-521271 | B2 | 4/2010 | |
| JP | 2016-537080 | A | 12/2016 | |
| JP | 6335261 | B1 | 5/2018 | |
| WO | WO 2008/097498 | A1 | 8/2008 | |
| WO | WO 2015/160348 | A1 | 10/2015 | |
| WO | WO-2017075532 | A1 * | 5/2017 | A61J 7/0053 |
| WO | WO 2017/192565 | A1 | 11/2017 | |
| WO | WO 2018/031239 | A1 | 2/2018 | |
| WO | WO 2018/232180 | A1 | 12/2018 | |

OTHER PUBLICATIONS

International Search Report and Written Opinion for International App. No. PCT/US2019/021904 mailed Jul. 7, 2019.
[No Author Listed], Vertex to Acquire ViaCyte, With the Goal of Accelerating its Potentially Curative VX-880 Programs in Type 1 Diabetes. Business Wire. Jul. 11, 2022. Accessible from < https://www.businesswire.com/news/home/20220711005280/en/> 2 pages.
[No Author Listed], A Hard Pill to Swallow? In Transit for a Couple of Years, FDA Finally Coughs Up Draft Guidance on Physical Attributes of Generic Tablets and Capsules. https://www.thefdalawblog.com/2013/12/a-hard-pill-to-swallow-in-transit-for-a-couple-of-years-fda-finally-coughs-up-draft-guidance-on-phys [last accessed Sep. 27, 2024].

* cited by examiner

IMPLANTATION DEVICES, SYSTEM, AND METHODS

CROSS-REFERENCE

This application is a national stage filing under 35 U.S.C. § 371 of International Patent Application Serial No. PCT/US2019/021904, filed Mar. 12, 2019, which claims the benefit of U.S. Provisional Application Ser. No. 62/642,529, filed Mar. 13, 2018, the contents of each of which are hereby incorporated by reference in their entirety herein.

BACKGROUND OF THE INVENTION

Therapeutic devices that deliver biological products can be used to treat metabolic disorders, such as diabetes. The therapeutic devices can be implantable to provide a biological product, such as insulin, for an extended period of time. The biological products can be delivered to a subject on or within a membrane, encapsulation chamber, or reservoir. To ensure proper delivery of the biological products into the subject, the membrane, encapsulation chamber, or reservoir is pliable to conform to a treatment surface. Precise and accurate placement of the biological products within the subject is vital to proper treatment.

SUMMARY OF THE INVENTION

One aspect provided herein is a device for delivering cells or therapeutics to a subject, the system comprising: a first elongate body comprising a proximal portion, a distal portion, and an open volume configured to hold the cells or therapeutics, wherein the open volume leads to an opening at the distal portion, wherein the opening comprises a dimension equal to or greater than about 1 cm; a second elongate body comprising a proximal portion and a distal portion, wherein the distal portion of the second elongate body is sized to fit within the open volume of the first elongate body, and move relative to the first elongate body. In some embodiments, the first elongate body can be generally flat. In some embodiments, the system can comprise a volume equal to or less than about 40 cm^3. In some embodiments, a ratio of a width of the first elongate body to a height of the first elongate body can be equal to or greater than about 5:1. In some embodiments, the first elongate body can comprise a generally uniform width and height throughout. In some embodiments, the open volume can comprise a width generally equal to a width of the opening. In some embodiments, the open volume can comprise a uniform width. In some embodiments, the first elongate body can comprise a gripping surface designed to be gripped by an operator. In some embodiments, the second elongate body can comprise a gripping surface designed to be gripped by an operator. In some embodiments, the distal portion of the second elongate body can comprise a surface configured to contact the cells or therapeutics. In some embodiments, the first elongate body can comprise titanium. In some embodiments, the proximal portion of the first elongate body can be proximally located relative to the proximal portion of the second elongate body. In some embodiments, the second elongate body can comprise a cross sectional area generally equal to a cross sectional area of the open volume. In some embodiments, the system can comprise an average thickness equal to or less than about 1 cm. In some embodiments, the system can comprise an average thickness equal to or less than about 0.5 cm. In some embodiments, the system can comprise an average width equal to or less than about 5 cm. In some embodiments, the system can comprise a length equal to or less than about 30 cm.

One aspect provided herein is a system for delivering cells or therapeutics to a subject, the system comprising: a first elongate body comprising a proximal portion, a distal portion, and an open volume configured to hold the cells or therapeutics, wherein the open volume leads to an opening at the distal portion, wherein the opening comprises a dimension equal to or greater than about 1 cm; a second elongate body comprising a proximal portion and a distal portion, wherein the distal portion of the second elongate body is sized to fit within the open volume of the first elongate body, and move relative to the first elongate body. In some embodiments, the system can further comprise a membrane, encapsulation chamber, or reservoir in the open volume, wherein the membrane, encapsulation chamber, or reservoir comprises the cells or therapeutics. In some embodiments, the cells can be encapsulated within the membrane, encapsulation chamber, or reservoir. In some embodiments, the cells can be insulin producing cells. In some embodiments, a width of the membrane, encapsulation chamber, or reservoir can be equal to or greater than 70% of a width of the open volume. In some embodiments, the membrane, encapsulation chamber, or reservoir can be held in a frame. In some embodiments, the frame can be rigid or semi-rigid. In some embodiments, the frame can be a triplet frame configured to couple to a plurality of membranes, encapsulation chambers, or reservoirs. In some embodiments, the first elongate body can be generally flat. In some embodiments, the system can comprise a volume equal to or less than about 40 cm^3. In some embodiments, a ratio of a width of the first elongate body to a height of the first elongate body can be equal to or greater than about 5:1. In some embodiments, the first elongate body can comprise a generally uniform width and height throughout. In some embodiments, the open volume can comprise a width generally equal to a width of the opening. In some embodiments, the open volume can comprise a uniform width. In some embodiments, the first elongate body can comprise a gripping surface designed to be gripped by an operator. In some embodiments, the second elongate body can comprise a gripping surface designed to be gripped by an operator. In some embodiments, the distal portion of the second elongate body can comprise a surface configured to contact the cells or therapeutics. In some embodiments, the first elongate body can comprise titanium. In some embodiments, the proximal portion of the first elongate body can be proximally located relative to the proximal portion of the second elongate body. In some embodiments, the second elongate body can comprise a cross sectional area generally equal to a cross sectional area of the open volume. In some embodiments, the system can comprise an average thickness equal to or less than about 1 cm. In some embodiments, the system can comprise an average thickness equal to or less than about 0.5 cm. In some embodiments, the system can comprise an average width equal to or less than about 5 cm. In some embodiments, the system can comprise a length equal to or less than about 30 cm.

Another aspect provided herein is a method for delivering cells or therapeutics to a subject, the method comprising: directing the cells or therapeutics towards a delivery site; holding the cells or therapeutics at the delivery site, wherein the cells or therapeutics are held within an open volume of a first positioning body; withdrawing the first positioning body while the cells or therapeutics are held at the delivery site; and delivering the cells or therapeutics to the subject. In some embodiments, the delivery site can be an implantation site for the cells or therapeutics. In some embodiments, the implantation site can be a subcutaneous or pre-peritoneal implantation site. In some embodiments, directing the cells or therapeutics towards the delivery site can comprise directing the first positioning body towards the delivery site with the cells or therapeutics held within the open volume of the first positioning body. In some embodiments, directing the cells or therapeutics towards the delivery site can comprise directing the cells or therapeutics to the open volume of the first positioning body via a delivery instrument. In some embodiments, withdrawing the first positioning body while the cells or therapeutics are held at the delivery site further can comprise preventing or obstructing movement of the cells or therapeutics with a second positioning body while withdrawing the first positioning body. In some embodiments, the second positioning body can be positioned within the open volume of the first positioning body. In some embodiments, withdrawing the first positioning body while the cells or therapeutics are held to the delivery site can comprise relative movement of the cells or therapeutics out of the first positioning body via an opening of the first positioning body. In some embodiments, the method can comprise compressing the cells or therapeutics between tissue surfaces as the first positioning body is withdrawn. In some embodiments, the method can allow delivery of the cells or therapeutics to the subject without the cells or therapeutics experiencing unprotected positive pressure. In some embodiments, the first positioning body can comprise titanium. In some embodiments, the cells or therapeutics can be held in a membrane, encapsulation chamber, or reservoir. In some embodiments, the cells or therapeutics can be encapsulated in a membrane, encapsulation chamber, or reservoir. In some embodiments, the cells can be insulin producing cells. In some embodiments, the membrane, encapsulation chamber, or reservoir can be held in a frame. In some embodiments, the frame can be rigid or semi-rigid. In some embodiments, the frame can be a triplet frame configured to couple to a plurality of membranes, encapsulation chambers, or reservoirs.

In some embodiments, the opening can comprise a dimension of about 1 cm to about 5 cm. In some embodiments, the opening can comprise a dimension of at least about 1 cm. In some embodiments, the opening can comprise a dimension of at most about 5 cm. In some embodiments, the opening can comprise a dimension of about 1 cm to about 2 cm, about 1 cm to about 3 cm, about 1 cm to about 4 cm, about 1 cm to about 5 cm, about 2 cm to about 3 cm, about 2 cm to about 4 cm, about 2 cm to about 5 cm, about 3 cm to about 4 cm, about 3 cm to about 5 cm, or about 4 cm to about 5 cm. In some embodiments, the opening can comprise a dimension of about 1 cm, about 2 cm, about 3 cm, about 4 cm, or about 5 cm.

In some embodiments, a width of the membrane, encapsulation chamber, or reservoir can be greater than a width of the open volume by about 70% to about 95%. In some embodiments, a width of the membrane, encapsulation chamber, or reservoir can be greater than a width of the open volume by at least about 70%. In some embodiments, a width of the membrane, encapsulation chamber, or reservoir can be greater than a width of the open volume by at most about 95%. In some embodiments, a width of the membrane, encapsulation chamber, or reservoir can be greater than a width of the open volume by about 70% to about 75%, about 70% to about 80%, about 70% to about 85%, about 70% to about 90%, about 70% to about 95%, about 75% to about 80%, about 75% to about 85%, about 75% to about 90%, about 75% to about 95%, about 80% to about 85%, about 80% to about 90%, about 80% to about 95%, about 85% to about 90%, about 85% to about 95%, or about 90% to about 95%. In some embodiments, a width of the membrane, encapsulation chamber, or reservoir can be greater than a width of the open volume by about 70%, about 75%, about 80%, about 85%, about 90%, or about 95%.

In some embodiments, the system can comprise a volume of about 15 cm$^3$ to about 40 cm$^3$. In some embodiments, the system can comprise a volume of at least about 15 cm$^3$. In some embodiments, the system can comprise a volume of at most about 40 cm$^3$. In some embodiments, the system can comprise a volume of about 40 cm$^3$ to about 35 cm$^3$, about 40 cm$^3$ to about 30 cm$^3$, about 40 cm$^3$ to about 25 cm$^3$, about 40 cm$^3$ to about 20 cm$^3$, about 40 cm$^3$ to about 15 cm$^3$, about 35 cm$^3$ to about 30 cm$^3$, about 35 cm$^3$ to about 25 cm$^3$, about 35 cm$^3$ to about 20 cm$^3$, about 35 cm$^3$ to about 15 cm$^3$, about 30 cm$^3$ to about 25 cm$^3$, about 30 cm$^3$ to about 20 cm$^3$, about 30 cm$^3$ to about 15 cm$^3$, about 25 cm$^3$ to about 20 cm$^3$, about 25 cm$^3$ to about 15 cm$^3$, or about 20 cm$^3$ to about 15 cm$^3$. In some embodiments, the system can comprise a volume of about 40 cm$^3$, about 35 cm$^3$, about 30 cm$^3$, about 25 cm$^3$, about 20 cm$^3$, or about 15 cm$^3$.

In some embodiments, a ratio of a width of the first elongate body to a height of the first elongate body can be about 5:1 to about 10:1. In some embodiments, a ratio of a width of the first elongate body to a height of the first elongate body can be at least about 5:1. In some embodiments, a ratio of a width of the first elongate body to a height of the first elongate body can be at most about 10:1. In some embodiments, a ratio of a width of the first elongate body to a height of the first elongate body can be about 5:1 to about 5.5:1, about 5:1 to about 6:1, about 5:1 to about 6.5:1, about 5:1 to about 7:1, about 5:1 to about 7.5:1, about 5:1 to about 8:1, about 5:1 to about 9:1, about 5:1 to about 10:1, about 5.5:1 to about 6:1, about 5.5:1 to about 6.5:1, about 5.5:1 to about 7:1, about 5.5:1 to about 7.5:1, about 5.5:1 to about 8:1, about 5.5:1 to about 9:1, about 5.5:1 to about 10:1, about 6:1 to about 6.5:1, about 6:1 to about 7:1, about 6:1 to about 7.5:1, about 6:1 to about 8:1, about 6:1 to about 9:1, about 6:1 to about 10:1, about 6.5:1 to about 7:1, about 6.5:1 to about 7.5:1, about 6.5:1 to about 8:1, about 6.5:1 to about 9:1, about 6.5:1 to about 10:1, about 7:1 to about 7.5:1, about 7:1 to about 8:1, about 7:1 to about 9:1, about 7:1 to about 10:1, about 7.5:1 to about 8:1, about 7.5:1 to about 9:1, about 7.5:1 to about 10:1, about 8:1 to about 9:1, about 8:1 to about 10:1, or about 9:1 to about 10:1. In some embodiments, a ratio of a width of the first elongate body to a height of the first elongate body can be about 5:1, about 5.5:1, about 6:1, about 6.5:1, about 7:1, about 7.5:1, about 8:1, about 9:1, or about 10:1.

In some embodiments, the average thickness can be about 0.2 cm to about 1 cm. In some embodiments, the average thickness can be at least about 0.2 cm. In some embodiments, the average thickness can be at most about 1 cm. In some embodiments, the average thickness can be about 0.2 cm to about 0.3 cm, about 0.2 cm to about 0.4 cm, about 0.2 cm to about 0.5 cm, about 0.2 cm to about 0.6 cm, about 0.2 cm to about 0.7 cm, about 0.2 cm to about 0.8 cm, about 0.2 cm to about 0.9 cm, about 0.2 cm to about 1 cm, about 0.3 cm to about 0.4 cm, about 0.3 cm to about 0.5 cm, about 0.3 cm to about 0.6 cm, about 0.3 cm to about 0.7 cm, about 0.3 cm to about 0.8 cm, about 0.3 cm to about 0.9 cm, about 0.3 cm to about 1 cm, about 0.4 cm to about 0.5 cm, about 0.4 cm to about 0.6 cm, about 0.4 cm to about 0.7 cm, about 0.4 cm to about 0.8 cm, about 0.4 cm to about 0.9 cm, about 0.4 cm to about 1 cm, about 0.5 cm to about 0.6 cm, about 0.5 cm to about 0.7 cm, about 0.5 cm to about 0.8 cm, about 0.5 cm to about 0.9 cm, about 0.5 cm to about 1 cm, about 0.6 cm to about 0.7 cm, about 0.6 cm to about 0.8 cm, about 0.6 cm to about 0.9 cm, about 0.6 cm to about 1 cm, about 0.7 cm to about 0.8 cm, about 0.7 cm to about 0.9 cm, about 0.7 cm to about 1 cm, about 0.8 cm to about 0.9 cm, about 0.8 cm to about 1 cm, or about 0.9 cm to about 1 cm. In some embodiments, the average thickness is about 0.2 cm, about 0.3 cm, about 0.4 cm, about 0.5 cm, about 0.6 cm, about 0.7 cm, about 0.8 cm, about 0.9 cm, or about 1 cm.

Another aspect provided herein is a membrane, encapsulation chamber, or reservoir implantation device comprising: a first elongate body comprising an elongated hollow body comprising an open volume having a distal aperture and a proximal aperture, wherein at least one of the open volume, the distal aperture and the proximal aperture are configured to receive a membrane, encapsulation chamber, or reservoir; and a second elongate body configured to fit within the open volume of the first elongate body and to prevent translation of the membrane, encapsulation chamber, or reservoir in a direction from the distal aperture to the proximal aperture. In some embodiments, the open volume can have a width of about 0.2 cm to about 10 cm. In some embodiments, the open volume can have a height of about 0.01 cm to about 5 cm. In some embodiments, the open volume can have a length of about 5 cm to about 30 cm. In some embodiments, the first elongate body can have a width of about 0.75 cm to about 3 cm. In some embodiments, the first elongate body can have a height of about 0.05 cm to about 3 cm. In some embodiments, at least one of the proximal portion and the distal portion of the first elongate body can have a height of about 0.05 cm to about 3 cm. In some embodiments, the first elongate body can have a length of about 5 cm to about 30 cm. In some embodiments, the elongated shaft can have a height of about 0.01 cm to about 5 cm. In some embodiments, the elongated shaft can have a length of about 5 cm to about 30 cm. In some embodiments, the elongated shaft can have a width of about 0.75 cm to about 3 cm. In some embodiments, the width of the first elongate body can be greater than the width of the open volume by about 1% to about 50%. In some embodiments, the height of the first elongate body can be greater than the width of the open volume by about 1% to about 50%. In some embodiments, the length of the first elongate body can be greater than the length of the open volume by at most about 50%. In some embodiments, the width of the first elongate body can be greater than the height of the first elongate body by about 1% to about 5000%. In some embodiments, the width of the open volume can be greater than the height of the open volume by about 1% to about 5000%. In some embodiments, the height of the open volume of the first elongate body can be greater than the height of the elongated shaft by about 1% to about 30%. In some embodiments, the width of the open volume of the first elongate body can be greater than the width of the elongated shaft by about 1% to about 30%. In some embodiments, the width of the elongated shaft can be greater than the height of the elongated shaft by about 1% to about 5000%. In some embodiments, at least one of the open volume and the elongated shaft can have a normal cross-sectional shape comprising a circle, an oval, an ellipse, a triangle, a square, a regular polygon, an irregular polygon, or any combination thereof. In some embodiments, at least one of the open volume and the elongated shaft can be generally straight in a direction from the proximal portion to the distal portion. In some embodiments, the centroids of the cross sections of least one of the open volume and the elongated shaft in a direction from the proximal portion to the distal portion can form a line or a continuous curve, or both. In some embodiments, the distal portion of the first elongate body can comprise at least one of a fillet and a chamfer. In some embodiments, the first elongate body can further comprise a first elongate body grip. In some embodiments, the second elongate body can further comprise a second elongate body grip. In some embodiments, the distal portion of the elongated shaft of the second elongate body can comprise a divot along the width of the elongated shaft. In some embodiments, the divot can be centered along the width of the elongated shaft. In some embodiments, the divot can comprise a concave radius. In some embodiments, at least one of the first elongate body and the second elongate body further can comprise a stop, wherein the stop is configured to maintain the second elongate body within the open volume of the first elongate body. In some embodiments, at least one of the first elongate body and the second elongate body can further comprise a bearing. In some embodiments, at least one of the first elongate body and the second elongate body can be composed of metal, plastic, carbon fiber, fiberglass, wood, ceramic, or any combination thereof. In some embodiments, at least one of the first elongate body and the second elongate body can be composed of titanium, aluminum, stainless steel, or any combination thereof.

Provided herein is a membrane, encapsulation chamber, or reservoir implantation system comprising: a membrane, encapsulation chamber, or reservoir; a first elongate body comprising an elongated hollow body comprising an open volume having a distal aperture and a proximal aperture, wherein at least one of the distal aperture and the proximal aperture are configured to receive the membrane, encapsulation chamber, or reservoir; and a second elongate body configured to fit within the open volume of the first elongate body and to prevent translation of the membrane, encapsulation chamber, or reservoir in a direction from the distal aperture to the proximal aperture. In some embodiments, the open volume can have a width of about 0.2 cm to about 10 cm. In some embodiments, the open volume can have a height of about 0.01 cm to about 5 cm. In some embodiments, the open volume can have a length of about 5 cm to about 30 cm. In some embodiments, the first elongate body can have a width of about 0.75 cm to about 3 cm. In some embodiments, the first elongate body can have a height of about 0.05 cm to about 3 cm. In some embodiments, at least one of the proximal portion and the distal portion of the first elongate body can have a height of about 0.05 cm to about 3 cm. In some embodiments, the first elongate body can have a length of about 5 cm to about 30 cm. In some embodiments, the elongated shaft can have a height of about 0.01 cm to about 5 cm. In some embodiments, the elongated shaft can have a length of about 5 cm to about 30 cm. In some embodiments, the elongated shaft can have a width of about 0.75 cm to about 3 cm. In some embodiments, the width of the first elongate body can be greater than the width of the open volume by about 1% to about 50%. In some embodiments, the height of the first elongate body can be greater than the width of the open volume by about 1% to about 50%. In some embodiments, the length of the first elongate body can be greater than the length of the open volume by at most about 50%. In some embodiments, the width of the first elongate body can be greater than the height of the first elongate body by about 1% to about 5000%. In some embodiments, the width of the open volume can be greater than the height of the open volume by about 1% to about 5000%. In some embodiments, the height of the open volume of the first elongate body can be greater than the height of the elongated shaft by about 1% to about 30%. In some embodiments, the width of the open volume of the first elongate body can be greater than the width of the elongated shaft by about 1% to about 30%. In some embodiments, the width of the elongated shaft can be greater than the height of the elongated shaft by about 1% to about 5000%. In some embodiments, the width of the open volume of the first elongate body can be greater than a width of the membrane, encapsulation chamber, or reservoir by about 1% to about 40%. In some embodiments, the height of the open volume of the first elongate body can be greater than a height of the membrane, encapsulation chamber, or reservoir by about 1% to about 40%. In some embodiments, the length of the open volume of the first elongate body can be greater than a length of the membrane, encapsulation chamber, or reservoir by about 5% to about 500%. In some embodiments, at least one of the open volume and the elongated shaft can have a normal cross-sectional shape comprising a circle, an oval, an ellipse, a triangle, a square, a regular polygon, an irregular polygon, or any combination thereof. In some embodiments, at least one of the open volume and the elongated shaft can be generally straight in a direction from the proximal portion to the distal portion. In some embodiments, the centroids of the cross sections of least one of the open volume and the elongated shaft in a direction from the proximal portion to the distal portion can form a line or a continuous curve, or both. In some embodiments, the distal portion of the first elongate body can comprise at least one of a fillet and a chamfer. In some embodiments, the first elongate body can further comprise a first elongate body grip. In some embodiments, the second elongate body can further comprise a second elongate body grip. In some embodiments, the distal portion of the elongated shaft of the second elongate body can comprise a divot along the width of the elongated shaft. In some embodiments, the divot can be centered along the width of the elongated shaft. In some embodiments, the divot can comprise a concave radius. In some embodiments, at least one of the first elongate body and the second elongate body can further comprise a stop, wherein the stop is configured to maintain the second elongate body within the open volume of the first elongate body. In some embodiments, at least one of the first elongate body and the second elongate body can further comprise a bearing. In some embodiments, at least one of the first elongate body and the second elongate body can be composed of metal, plastic, carbon fiber, fiberglass, wood, ceramic, or any combination thereof. In some embodiments, at least one of the first elongate body and the second elongate body can be composed of titanium, aluminum, stainless steel, or any combination thereof. Optionally, in some embodiments, the membrane, encapsulation chamber, or reservoir comprises a cell. In some embodiments, the cells can be configured to produce insulin. In some embodiments, the membrane can comprise a frame. In some embodiments, the membrane, encapsulation chamber, or reservoir can comprise 1, 2, 3, or more membranes, encapsulation chambers, or reservoirs. In some embodiments, the membrane, encapsulation chamber, or reservoir can comprise 1, 2, 3, or more membranes, encapsulation chambers, or reservoirs in a single frame. In some embodiments, the system can further comprise a membrane, encapsulation chamber, or reservoir stand configured to temporarily affix the membrane, encapsulation chamber, or reservoir. In some embodiments, the membrane, encapsulation chamber, or reservoir stand can be configured to temporarily affix the membrane, encapsulation chamber, or reservoir during the insertion of the membrane, encapsulation chamber, or reservoir into the first elongate body. In some embodiments, the membrane, encapsulation chamber, or reservoir stand can comprise a clip configured to temporarily affix the membrane, encapsulation chamber, or reservoir to the stand. In some embodiments, the membrane, encapsulation chamber, or reservoir stand can further comprise a cover configured to cover the membrane on the stand. In some embodiments, the cover can be further configured to seal the membrane, encapsulation chamber, or reservoir within the membrane, encapsulation chamber, or reservoir stand. In some embodiments, the membrane, encapsulation chamber, or reservoir stand can comprise a 1, 2, 3, or more clips. In some embodiments, the membrane, encapsulation chamber, or reservoir stand can comprise a base connected to the clip and configured stabilize the clip on a surface. In some embodiments, the membrane, encapsulation chamber, or reservoir stand can comprise a ledge attached to the base and configured to support a bottom side of the membrane, encapsulation chamber, or reservoir against the clip. In some embodiments, the membrane, encapsulation chamber, or reservoir stand can comprise a 1, 2, 3, or more ledges. In some embodiments, at least one of the membrane, encapsulation chamber, or reservoir stand, the clip, the ledge, the cover, and the base can be composed of metal, plastic, carbon fiber, fiberglass, wood, ceramic, or any combination thereof.

Another aspect provided herein is a method for subcutaneously delivering therapeutic comprising: placing a membrane, encapsulation chamber, or reservoir through a distal aperture or a proximal aperture of a membrane, encapsulation chamber, or reservoir implantation device, the device comprising a second elongate body and a first elongate body comprising an elongated hollow body having an open volume; subcutaneously inserting the distal portion of the first elongate body into a subject; and translating the first elongate body relative to the second elongate body in a direction from the distal aperture to the proximal aperture, to remove the first elongate body from the subject while maintaining the position of at least one of the membrane, encapsulation chamber, or reservoir and the second elongate body with respect to the subject. In some embodiments, the open volume can have a width of about 0.2 cm to about 10 cm. In some embodiments, the open volume can have a height of about 0.01 cm to about 5 cm. In some embodiments, the open volume can have a length of about 5 cm to about 30 cm. In some embodiments, the first elongate body can have a width of about 0.75 cm to about 3 cm. In some embodiments, the first elongate body can have a height of about 0.05 cm to about 3 cm. In some embodiments, at least one of the proximal portion and the distal portion of the first elongate body can have a height of about 0.05 cm to about 3 cm. In some embodiments, the first elongate body can have a length of about 5 cm to about 30 cm. In some embodiments, the elongated shaft can have a height of about 0.01 cm to about 5 cm. In some embodiments, the elongated shaft can have a length of about 5 cm to about 30 cm. In some embodiments, the elongated shaft can have a width of about 0.2 cm to about 10 cm. In some embodiments, the width of the first elongate body can have greater than the width of the open volume by about 1% to about 50%. In some embodiments, the height of the first elongate body can have greater than the width of the open volume by about 1% to about 50%. In some embodiments, the length of the first elongate body can have greater than the length of the open volume by at most about 50%. In some embodiments, the width of the first elongate body can have greater than the height of first elongate body by about 1% to about 5000%. In some embodiments, the width of the open volume can be greater than the height of the open volume by about 1% to about 5000%. In some embodiments, the height of the open volume of the first elongate body can be greater than the height of the elongated shaft by about 1% to about 30%. In some embodiments, the width of the open volume of the first elongate body can be greater than the width of the elongated shaft by about 1% to about 30%. In some embodiments, the width of the elongated shaft can be greater than the height of the elongated shaft by about 1% to about 5000%. In some embodiments, the width of the open volume of the first elongate body can be greater than a width of the membrane, encapsulation chamber, or reservoir by about 1% to about 40%. In some embodiments, the height of the open volume of the first elongate body can be greater than a height of the membrane, encapsulation chamber, or reservoir by about 1% to about 40%. In some embodiments, the length of the open volume of the first elongate body can be greater than a length of the membrane, encapsulation chamber, or reservoir by about 5% to about 500%. In some embodiments, at least one of the open volume and the elongated shaft can have a normal cross-sectional shape comprising a circle, an oval, an ellipse, a triangle, a square, a regular polygon, an irregular polygon, or any combination thereof. In some embodiments, at least one of the open volume and the elongated shaft can be generally straight in a direction from the proximal portion to the distal portion. In some embodiments, the centroids of the cross sections of least one of the open volume and the elongated shaft in a direction from the proximal portion to the distal portion can form a line or a continuous curve, or both. In some embodiments, the distal portion of the first elongate body can comprise at least one of a fillet and a chamfer. In some embodiments, the first elongate body can further comprise a first elongate body grip. In some embodiments, the second elongate body can further comprise a second elongate body grip. In some embodiments, the distal portion of the elongated shaft of the second elongate body can comprise a divot along the width of the elongated shaft. In some embodiments, the divot can be centered along the width of the elongated shaft. In some embodiments, the divot can comprise a concave radius. In some embodiments, at least one of the first elongate body and the second elongate body further can comprise a stop, wherein the stop is configured to maintain the second elongate body within the open volume of the first elongate body. In some embodiments, at least one of the first elongate body and the second elongate body can further comprise a bearing. In some embodiments, at least one of the first elongate body and the second elongate body can be composed of metal, plastic, carbon fiber, fiberglass, wood, ceramic, or any combination thereof. In some embodiments, at least one of the first elongate body and the second elongate body can be composed of titanium, aluminum, stainless steel, or any combination thereof. In some embodiments, the membrane, encapsulation chamber, or reservoir can comprise a cell. In some embodiments, the cells can be configured to produce insulin. In some embodiments, the membrane, encapsulation chamber, or reservoir can comprise a frame. In some embodiments, the membrane, encapsulation chamber, or reservoir can comprise 1, 2, 3, or more membranes, encapsulation chambers, or reservoirs. In some embodiments, the membrane, encapsulation chamber, or reservoir can comprise 1, 2, 3, or more membranes, encapsulation chambers, or reservoirs in a single frame. In some embodiments, the method can further comprise a membrane, encapsulation chamber, or reservoir stand configured to temporarily affix the membrane, encapsulation chamber, or reservoir. In some embodiments, the membrane, encapsulation chamber, or reservoir stand can be configured to temporarily affix the membrane, encapsulation chamber, or reservoir during the insertion of the membrane, encapsulation chamber, or reservoir into the first elongate body. In some embodiments, the membrane, encapsulation chamber, or reservoir stand can comprise a clip configured to temporarily affix the membrane, encapsulation chamber, or reservoir to the stand. In some embodiments, the membrane, encapsulation chamber, or reservoir stand can comprise a 1, 2, 3, or more clips. In some embodiments, the membrane, encapsulation chamber, or reservoir stand can comprise a base connected to the clip and configured stabilize the clip on a surface. In some embodiments, the membrane, encapsulation chamber, or reservoir stand can comprise a ledge attached to the base and configured to support a bottom side of the membrane, encapsulation chamber, or reservoir against the clip. In some embodiments, the membrane, encapsulation chamber, or reservoir stand can comprise a 1, 2, 3, or more ledges. In some embodiments, the method can further comprise placing the membrane, encapsulation chamber, or reservoir on a membrane, encapsulation chamber, or reservoir stand before placing the membrane, encapsulation chamber, or reservoir through the distal aperture or the proximal aperture of the first elongate body. In some embodiments, the method can further comprise compressing a clip against the membrane, encapsulation chamber, or reservoir. In some embodiments, the method can further comprise decompressing the clip from the membrane, encapsulation chamber, or reservoir once the membrane, encapsulation chamber, or reservoir is placed through the distal aperture or the proximal aperture of the first elongate body. In some embodiments, the membrane stand can be configured to temporarily affix the membrane, encapsulation chamber, or reservoir to insert the membrane, encapsulation chamber, or reservoir into the first elongate body. In some embodiments, the method can further comprise removing the first elongate body and the second elongate body from the subject.

In some embodiments, the open volume can have a width of about 0.75 cm to about 3 cm. In some embodiments, the open volume can have a width of at least about 0.75 cm. In some embodiments, the open volume can have a width of at most about 3 cm. In some embodiments, the open volume can have a width of about 0.75 cm to about 1 cm, about 0.75 cm to about 1.25 cm, about 0.75 cm to about 1.5 cm, about 0.75 cm to about 1.75 cm, about 0.75 cm to about 2 cm, about 0.75 cm to about 2.25 cm, about 0.75 cm to about 2.5 cm, about 0.75 cm to about 2.75 cm, about 0.75 cm to about 3 cm, about 1 cm to about 1.25 cm, about 1 cm to about 1.5 cm, about 1 cm to about 1.75 cm, about 1 cm to about 2 cm, about 1 cm to about 2.25 cm, about 1 cm to about 2.5 cm, about 1 cm to about 2.75 cm, about 1 cm to about 3 cm, about 1.25 cm to about 1.5 cm, about 1.25 cm to about 1.75 cm, about 1.25 cm to about 2 cm, about 1.25 cm to about 2.25 cm, about 1.25 cm to about 2.5 cm, about 1.25 cm to about 2.75 cm, about 1.25 cm to about 3 cm, about 1.5 cm to about 1.75 cm, about 1.5 cm to about 2 cm, about 1.5 cm to about 2.25 cm, about 1.5 cm to about 2.5 cm, about 1.5 cm to about 2.75 cm, about 1.5 cm to about 3 cm, about 1.75 cm to about 2 cm, about 1.75 cm to about 2.25 cm, about 1.75 cm to about 2.5 cm, about 1.75 cm to about 2.75 cm, about 1.75 cm to about 3 cm, about 2 cm to about 2.25 cm, about 2 cm to about 2.5 cm, about 2 cm to about 2.75 cm, about 2 cm to about 3 cm, about 2.25 cm to about 2.5 cm, about 2.25 cm to about 2.75 cm, about 2.25 cm to about 3 cm, about 2.5 cm to about 2.75 cm, about 2.5 cm to about 3 cm, or about 2.75 cm to about 3 cm. In some embodiments, the open volume can have a width of about 0.75 cm, about 1 cm, about 1.25 cm, about 1.5 cm, about 1.75 cm, about 2 cm, about 2.25 cm, about 2.5 cm, about 2.75 cm, or about 3 cm.

In some embodiments, the open volume can have a height of about 0.01 cm to about 5 cm. In some embodiments, the open volume can have a height of at least about 0.01 cm. In some embodiments, the open volume can have a height of at most about 5 cm. In some embodiments, the open volume can have a height of about 0.01 cm to about 0.02 cm, about 0.01 cm to about 0.05 cm, about 0.01 cm to about 0.1 cm, about 0.01 cm to about 0.2 cm, about 0.01 cm to about 0.5 cm, about 0.01 cm to about 1 cm, about 0.01 cm to about 2 cm, about 0.01 cm to about 3 cm, about 0.01 cm to about 4 cm, about 0.01 cm to about 5 cm, about 0.02 cm to about 0.05 cm, about 0.02 cm to about 0.1 cm, about 0.02 cm to about 0.2 cm, about 0.02 cm to about 0.5 cm, about 0.02 cm to about 1 cm, about 0.02 cm to about 2 cm, about 0.02 cm to about 3 cm, about 0.02 cm to about 4 cm, about 0.02 cm to about 5 cm, about 0.05 cm to about 0.1 cm, about 0.05 cm to about 0.2 cm, about 0.05 cm to about 0.5 cm, about 0.05 cm to about 1 cm, about 0.05 cm to about 2 cm, about 0.05 cm to about 3 cm, about 0.05 cm to about 4 cm, about 0.05 cm to about 5 cm, about 0.1 cm to about 0.2 cm, about 0.1 cm to about 0.5 cm, about 0.1 cm to about 1 cm, about 0.1 cm to about 2 cm, about 0.1 cm to about 3 cm, about 0.1 cm to about 4 cm, about 0.1 cm to about 5 cm, about 0.2 cm to about 0.5 cm, about 0.2 cm to about 1 cm, about 0.2 cm to about 2 cm, about 0.2 cm to about 3 cm, about 0.2 cm to about 4 cm, about 0.2 cm to about 5 cm, about 0.5 cm to about 1 cm, about 0.5 cm to about 2 cm, about 0.5 cm to about 3 cm, about 0.5 cm to about 4 cm, about 0.5 cm to about 5 cm, about 1 cm to about 2 cm, about 1 cm to about 3 cm, about 1 cm to about 4 cm, about 1 cm to about 5 cm, about 2 cm to about 3 cm, about 2 cm to about 4 cm, about 2 cm to about 5 cm, about 3 cm to about 4 cm, about 3 cm to about 5 cm, or about 4 cm to about 5 cm. In some embodiments, the open volume can have a height of about 0.01 cm, about 0.02 cm, about 0.05 cm, about 0.1 cm, about 0.2 cm, about 0.5 cm, about 1 cm, about 2 cm, about 3 cm, about 4 cm, or about 5 cm.

In some embodiments, the open volume can have a length of about 5 cm to about 30 cm. In some embodiments, the open volume can have a length of at least about 5 cm. In some embodiments, the open volume can have a length of at most about 30 cm. In some embodiments, the open volume can have a length of about 5 cm to about 6 cm, about 5 cm to about 8 cm, about 5 cm to about 10 cm, about 5 cm to about 15 cm, about 5 cm to about 20 cm, about 5 cm to about 25 cm, about 5 cm to about 30 cm, about 6 cm to about 8 cm, about 6 cm to about 10 cm, about 6 cm to about 15 cm, about 6 cm to about 20 cm, about 6 cm to about 25 cm, about 6 cm to about 30 cm, about 8 cm to about 10 cm, about 8 cm to about 15 cm, about 8 cm to about 20 cm, about 8 cm to about 25 cm, about 8 cm to about 30 cm, about 10 cm to about 15 cm, about 10 cm to about 20 cm, about 10 cm to about 25 cm, about 10 cm to about 30 cm, about 15 cm to about 20 cm, about 15 cm to about 25 cm, about 15 cm to about 30 cm, about 20 cm to about 25 cm, about 20 cm to about 30 cm, or about 25 cm to about 30 cm. In some embodiments, the open volume can have a length of about 5 cm, about 6 cm, about 8 cm, about 10 cm, about 15 cm, about 20 cm, about 25 cm, or about 30 cm.

In some embodiments, the first elongate body can have a width of about 0.75 cm to about 3 cm. In some embodiments, the first elongate body can have a width of at least about 0.75 cm. In some embodiments, the first elongate body can have a width of at most about 3 cm. In some embodiments, the first elongate body can have a width of about 0.75 cm to about 1 cm, about 0.75 cm to about 1.25 cm, about 0.75 cm to about 1.5 cm, about 0.75 cm to about 1.75 cm, about 0.75 cm to about 2 cm, about 0.75 cm to about 2.25 cm, about 0.75 cm to about 2.5 cm, about 0.75 cm to about 2.75 cm, about 0.75 cm to about 3 cm, about 1 cm to about 1.25 cm, about 1 cm to about 1.5 cm, about 1 cm to about 1.75 cm, about 1 cm to about 2 cm, about 1 cm to about 2.25 cm, about 1 cm to about 2.5 cm, about 1 cm to about 2.75 cm, about 1 cm to about 3 cm, about 1.25 cm to about 1.5 cm, about 1.25 cm to about 1.75 cm, about 1.25 cm to about 2 cm, about 1.25 cm to about 2.25 cm, about 1.25 cm to about 2.5 cm, about 1.25 cm to about 2.75 cm, about 1.25 cm to about 3 cm, about 1.5 cm to about 1.75 cm, about 1.5 cm to about 2 cm, about 1.5 cm to about 2.25 cm, about 1.5 cm to about 2.5 cm, about 1.5 cm to about 2.75 cm, about 1.5 cm to about 3 cm, about 1.75 cm to about 2 cm, about 1.75 cm to about 2.25 cm, about 1.75 cm to about 2.5 cm, about 1.75 cm to about 2.75 cm, about 1.75 cm to about 3 cm, about 2 cm to about 2.25 cm, about 2 cm to about 2.5 cm, about 2 cm to about 2.75 cm, about 2 cm to about 3 cm, about 2.25 cm to about 2.5 cm, about 2.25 cm to about 2.75 cm, about 2.25 cm to about 3 cm, about 2.5 cm to about 2.75 cm, about 2.5 cm to about 3 cm, or about 2.75 cm to about 3 cm. In some embodiments, the first elongate body can have a width of about 0.75 cm, about 1 cm, about 1.25 cm, about 1.5 cm, about 1.75 cm, about 2 cm, about 2.25 cm, about 2.5 cm, about 2.75 cm, or about 3 cm.

In some embodiments, the first elongate body can have a height of about 0.01 cm to about 3 cm. In some embodiments, the first elongate body can have a height of at least about 0.01 cm. In some embodiments, the first elongate body can have a height of at most about 3 cm. In some embodiments, the first elongate body can have a height of about 0.05 cm to about 0.01 cm, about 0.05 cm to about 0.02 cm, about 0.05 cm to about 0.05 cm, about 0.05 cm to about 0.1 cm, about 0.05 cm to about 0.2 cm, about 0.05 cm to about 0.5 cm, about 0.05 cm to about 1 cm, about 0.05 cm to about 2 cm, about 0.05 cm to about 3 cm, about 0.01 cm to about 0.02 cm, about 0.01 cm to about 0.05 cm, about 0.01 cm to about 0.1 cm, about 0.01 cm to about 0.2 cm, about 0.01 cm to about 0.5 cm, about 0.01 cm to about 1 cm, about 0.01 cm to about 2 cm, about 0.01 cm to about 3 cm, about 0.02 cm to about 0.05 cm, about 0.02 cm to about 0.1 cm, about 0.02 cm to about 0.2 cm, about 0.02 cm to about 0.5 cm, about 0.02 cm to about 1 cm, about 0.02 cm to about 2 cm, about 0.02 cm to about 3 cm, about 0.05 cm to about 0.1 cm, about 0.05 cm to about 0.2 cm, about 0.05 cm to about 0.5 cm, about 0.05 cm to about 1 cm, about 0.05 cm to about 2 cm, about 0.05 cm to about 3 cm, about 0.1 cm to about 0.2 cm, about 0.1 cm to about 0.5 cm, about 0.1 cm to about 1 cm, about 0.1 cm to about 2 cm, about 0.1 cm to about 3 cm, about 0.2 cm to about 0.5 cm, about 0.2 cm to about 1 cm, about 0.2 cm to about 2 cm, about 0.2 cm to about 3 cm, about 0.5 cm to about 1 cm, about 0.5 cm to about 2 cm, about 0.5 cm to about 3 cm, about 1 cm to about 2 cm, about 1 cm to about 3 cm, or about 2 cm to about 3 cm. In some embodiments, the first elongate body can have a height of about 0.05 cm, about 0.01 cm, about 0.02 cm, about 0.05 cm, about 0.1 cm, about 0.2 cm, about 0.5 cm, about 1 cm, about 2 cm, or about 3 cm.

In some embodiments, at least one of the proximal portion and the distal portion of the first elongate body can have a height of about 0.01 cm to about 3 cm. In some embodiments, at least one of the proximal portion and the distal portion of the first elongate body can have a height of at least about 0.01 cm. In some embodiments, at least one of the proximal portion and the distal portion of the first elongate body can have a height of at most about 3 cm. In some embodiments, at least one of the proximal portion and the distal portion of the first elongate body can have a height of about 0.05 cm to about 0.01 cm, about 0.05 cm to about 0.02 cm, about 0.05 cm to about 0.05 cm, about 0.05 cm to about 0.1 cm, about 0.05 cm to about 0.2 cm, about 0.05 cm to about 0.5 cm, about 0.05 cm to about 1 cm, about 0.05 cm to about 2 cm, about 0.05 cm to about 3 cm, about 0.01 cm to about 0.02 cm, about 0.01 cm to about 0.05 cm, about 0.01 cm to about 0.1 cm, about 0.01 cm to about 0.2 cm, about 0.01 cm to about 0.5 cm, about 0.01 cm to about 1 cm, about 0.01 cm to about 2 cm, about 0.01 cm to about 3 cm, about 0.02 cm to about 0.05 cm, about 0.02 cm to about 0.1 cm, about 0.02 cm to about 0.2 cm, about 0.02 cm to about 0.5 cm, about 0.02 cm to about 1 cm, about 0.02 cm to about 2 cm, about 0.02 cm to about 3 cm, about 0.05 cm to about 0.1 cm, about 0.05 cm to about 0.2 cm, about 0.05 cm to about 0.5 cm, about 0.05 cm to about 1 cm, about 0.05 cm to about 2 cm, about 0.05 cm to about 3 cm, about 0.1 cm to about 0.2 cm, about 0.1 cm to about 0.5 cm, about 0.1 cm to about 1 cm, about 0.1 cm to about 2 cm, about 0.1 cm to about 3 cm, about 0.2 cm to about 0.5 cm, about 0.2 cm to about 1 cm, about 0.2 cm to about 2 cm, about 0.2 cm to about 3 cm, about 0.5 cm to about 1 cm, about 0.5 cm to about 2 cm, about 0.5 cm to about 3 cm, about 1 cm to about 2 cm, about 1 cm to about 3 cm, or about 2 cm to about 3 cm. In some embodiments, at least one of the proximal portion and the distal portion of the first elongate body can have a height of about 0.05 cm, about 0.01 cm, about 0.02 cm, about 0.05 cm, about 0.1 cm, about 0.2 cm, about 0.5 cm, about 1 cm, about 2 cm, or about 3 cm.

In some embodiments, the first elongate body can have a length of about 5 cm to about 30 cm. In some embodiments, the first elongate body can have a length of at least about 5 cm. In some embodiments, the first elongate body can have a length of at most about 30 cm. In some embodiments, the first elongate body can have a length of about 5 cm to about 6 cm, about 5 cm to about 8 cm, about 5 cm to about 10 cm, about 5 cm to about 15 cm, about 5 cm to about 20 cm, about 5 cm to about 25 cm, about 5 cm to about 30 cm, about 6 cm to about 8 cm, about 6 cm to about 10 cm, about 6 cm to about 15 cm, about 6 cm to about 20 cm, about 6 cm to about 25 cm, about 6 cm to about 30 cm, about 8 cm to about 10 cm, about 8 cm to about 15 cm, about 8 cm to about 20 cm, about 8 cm to about 25 cm, about 8 cm to about 30 cm, about 10 cm to about 15 cm, about 10 cm to about 20 cm, about 10 cm to about 25 cm, about 10 cm to about 30 cm, about 15 cm to about 20 cm, about 15 cm to about 25 cm, about 15 cm to about 30 cm, about 20 cm to about 25 cm, about 20 cm to about 30 cm, or about 25 cm to about 30 cm. In some embodiments, the first elongate body can have a length of about 5 cm, about 6 cm, about 8 cm, about 10 cm, about 15 cm, about 20 cm, about 25 cm, or about 30 cm.

In some embodiments, the elongated shaft can have a height of about 0.01 cm to about 3 cm. In some embodiments, the elongated shaft can have a height of at least about 0.01 cm. In some embodiments, the elongated shaft can have a height of at most about 3 cm. In some embodiments, the elongated shaft can have a height of about 0.05 cm to about 0.01 cm, about 0.05 cm to about 0.02 cm, about 0.05 cm to about 0.05 cm, about 0.05 cm to about 0.1 cm, about 0.05 cm to about 0.2 cm, about 0.05 cm to about 0.5 cm, about 0.05 cm to about 1 cm, about 0.05 cm to about 2 cm, about 0.05 cm to about 3 cm, about 0.01 cm to about 0.02 cm, about 0.01 cm to about 0.05 cm, about 0.01 cm to about 0.1 cm, about 0.01 cm to about 0.2 cm, about 0.01 cm to about 0.5 cm, about 0.01 cm to about 1 cm, about 0.01 cm to about 2 cm, about 0.01 cm to about 3 cm, about 0.02 cm to about 0.05 cm, about 0.02 cm to about 0.1 cm, about 0.02 cm to about 0.2 cm, about 0.02 cm to about 0.5 cm, about 0.02 cm to about 1 cm, about 0.02 cm to about 2 cm, about 0.02 cm to about 3 cm, about 0.05 cm to about 0.1 cm, about 0.05 cm to about 0.2 cm, about 0.05 cm to about 0.5 cm, about 0.05 cm to about 1 cm, about 0.05 cm to about 2 cm, about 0.05 cm to about 3 cm, about 0.1 cm to about 0.2 cm, about 0.1 cm to about 0.5 cm, about 0.1 cm to about 1 cm, about 0.1 cm to about 2 cm, about 0.1 cm to about 3 cm, about 0.2 cm to about 0.5 cm, about 0.2 cm to about 1 cm, about 0.2 cm to about 2 cm, about 0.2 cm to about 3 cm, about 0.5 cm to about 1 cm, about 0.5 cm to about 2 cm, about 0.5 cm to about 3 cm, about 1 cm to about 2 cm, about 1 cm to about 3 cm, or about 2 cm to about 3 cm. In some embodiments, the elongated shaft can have a height of about 0.05 cm, about 0.01 cm, about 0.02 cm, about 0.05 cm, about 0.1 cm, about 0.2 cm, about 0.5 cm, about 1 cm, about 2 cm, or about 3 cm.

In some embodiments, the elongated shaft can have a width of about 0.75 cm to about 3 cm. In some embodiments, the elongated shaft can have a width of at least about 0.75 cm. In some embodiments, the elongated shaft can have a width of at most about 3 cm. In some embodiments, the elongated shaft can have a width of about 0.75 cm to about 1 cm, about 0.75 cm to about 1.25 cm, about 0.75 cm to about 1.5 cm, about 0.75 cm to about 1.75 cm, about 0.75 cm to about 2 cm, about 0.75 cm to about 2.25 cm, about 0.75 cm to about 2.5 cm, about 0.75 cm to about 2.75 cm, about 0.75 cm to about 3 cm, about 1 cm to about 1.25 cm, about 1 cm to about 1.5 cm, about 1 cm to about 1.75 cm, about 1 cm to about 2 cm, about 1 cm to about 2.25 cm, about 1 cm to about 2.5 cm, about 1 cm to about 2.75 cm, about 1 cm to about 3 cm, about 1.25 cm to about 1.5 cm, about 1.25 cm to about 1.75 cm, about 1.25 cm to about 2 cm, about 1.25 cm to about 2.25 cm, about 1.25 cm to about 2.5 cm, about 1.25 cm to about 2.75 cm, about 1.25 cm to about 3 cm, about 1.5 cm to about 1.75 cm, about 1.5 cm to about 2 cm, about 1.5 cm to about 2.25 cm, about 1.5 cm to about 2.5 cm, about 1.5 cm to about 2.75 cm, about 1.5 cm to about 3 cm, about 1.75 cm to about 2 cm, about 1.75 cm to about 2.25 cm, about 1.75 cm to about 2.5 cm, about 1.75 cm to about 2.75 cm, about 1.75 cm to about 3 cm, about 2 cm to about 2.25 cm, about 2 cm to about 2.5 cm, about 2 cm to about 2.75 cm, about 2 cm to about 3 cm, about 2.25 cm to about 2.5 cm, about 2.25 cm to about 2.75 cm, about 2.25 cm to about 3 cm, about 2.5 cm to about 2.75 cm, about 2.5 cm to about 3 cm, or about 2.75 cm to about 3 cm. In some embodiments, the elongated shaft can have a width of about 0.75 cm, about 1 cm, about 1.25 cm, about 1.5 cm, about 1.75 cm, about 2 cm, about 2.25 cm, about 2.5 cm, about 2.75 cm, or about 3 cm.

In some embodiments, the width of the first elongate body can be greater than the width of the open volume by about 1% to about 50%. In some embodiments, the width of the first elongate body can be greater than the width of the open volume by at least about 1%. In some embodiments, the width of the first elongate body can be greater than the width of the open volume by at most about 50%. In some embodiments, the width of the first elongate body can be greater than the width of the open volume by about 1% to about 2%, about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 2% to about 5%, about 2% to about 10%, about 2% to about 15%, about 2% to about 20%, about 2% to about 25%, about 2% to about 30%, about 2% to about 35%, about 2% to about 40%, about 2% to about 45%, about 2% to about 50%, about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 10% to about 15%, about 10% to about 20%, about 10% to about 25%, about 10% to about 30%, about 10% to about 35%, about 10% to about 40%, about 10% to about 45%, about 10% to about 50%, about 15% to about 20%, about 15% to about 25%, about 15% to about 30%, about 15% to about 35%, about 15% to about 40%, about 15% to about 45%, about 15% to about 50%, about 20% to about 25%, about 20% to about 30%, about 20% to about 35%, about 20% to about 40%, about 20% to about 45%, about 20% to about 50%, about 25% to about 30%, about 25% to about 35%, about 25% to about 40%, about 25% to about 45%, about 25% to about 50%, about 30% to about 35%, about 30% to about 40%, about 30% to about 45%, about 30% to about 50%, about 35% to about 40%, about 35% to about 45%, about 35% to about 50%, about 40% to about 45%, about 40% to about 50%, or about 45% to about 50%. In some embodiments, the width of the first elongate body can be greater than the width of the open volume by about 1%, about 2%, about 5%, about 10%, about 15%, about 20%, about 25%, about 30%, about 35%, about 40%, about 45%, or about 50%.

In some embodiments, the height of the first elongate body can be greater than the height of the open volume by about 1% to about 50%. In some embodiments, the height of the first elongate body can be greater than the height of the open volume by at least about 1%. In some embodiments, the height of the first elongate body can be greater than the height of the open volume by at most about 50%. In some embodiments, the height of the first elongate body can be greater than the height of the open volume by about 1% to about 2%, about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 2% to about 5%, about 2% to about 10%, about 2% to about 15%, about 2% to about 20%, about 2% to about 25%, about 2% to about 30%, about 2% to about 35%, about 2% to about 40%, about 2% to about 45%, about 2% to about 50%, about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 10% to about 15%, about 10% to about 20%, about 10% to about 25%, about 10% to about 30%, about 10% to about 35%, about 10% to about 40%, about 10% to about 45%, about 10% to about 50%, about 15% to about 20%, about 15% to about 25%, about 15% to about 30%, about 15% to about 35%, about 15% to about 40%, about 15% to about 45%, about 15% to about 50%, about 20% to about 25%, about 20% to about 30%, about 20% to about 35%, about 20% to about 40%, about 20% to about 45%, about 20% to about 50%, about 25% to about 30%, about 25% to about 35%, about 25% to about 40%, about 25% to about 45%, about 25% to about 50%, about 30% to about 35%, about 30% to about 40%, about 30% to about 45%, about 30% to about 50%, about 35% to about 40%, about 35% to about 45%, about 35% to about 50%, about 40% to about 45%, about 40% to about 50%, or about 45% to about 50%. In some embodiments, the height of the first elongate body can be greater than the height of the open volume by about 1%, about 2%, about 5%, about 10%, about 15%, about 20%, about 25%, about 30%, about 35%, about 40%, about 45%, or about 50%.

In some embodiments, the length of the first elongate body can be greater than the width of the open volume by at most about 50%, 40%, 30%, 20%, 10%, or 5%.

In some embodiments, the width of the first elongate body can be greater than the height of the first elongate body by about 1% to about 1,000%. In some embodiments, the width of the first elongate body can be greater than the height of the first elongate body by at least about 1%. In some embodiments, the width of the first elongate body can be greater than the height of the first elongate body by at most about 1,000%. In some embodiments, the width of the first elongate body can be greater than the height of the first elongate body by about 1% to about 2%, about 1% to about 5%, about 1% to about 10%, about 1% to about 20%, about 1% to about 50%, about 1% to about 100%, about 1% to about 200%, about 1% to about 500%, about 1% to about 1,000%, about 2% to about 5%, about 2% to about 10%, about 2% to about 20%, about 2% to about 50%, about 2% to about 100%, about 2% to about 200%, about 2% to about 500%, about 2% to about 1,000%, about 5% to about 10%, about 5% to about 20%, about 5% to about 50%, about 5% to about 100%, about 5% to about 200%, about 5% to about 500%, about 5% to about 1,000%, about 10% to about 20%, about 10% to about 50%, about 10% to about 100%, about 10% to about 200%, about 10% to about 500%, about 10% to about 1,000%, about 20% to about 50%, about 20% to about 100%, about 20% to about 200%, about 20% to about 500%, about 20% to about 1,000%, about 50% to about 100%, about 50% to about 200%, about 50% to about 500%, about 50% to about 1,000%, about 100% to about 200%, about 100% to about 500%, about 100% to about 1,000%, about 200% to about 500%, about 200% to about 1,000%, or about 500% to about 1,000%. In some embodiments, the width of the first elongate body can be greater than the height of the first elongate body by about 1%, about 2%, about 5%, about 10%, about 20%, about 50%, about 100%, about 200%, about 500%, or about 1,000%.

In some embodiments, the width of the open volume can be greater than the height of the open volume by about 1% to about 1,000%. In some embodiments, the width of the open volume can be greater than the height of the open volume by at least about 1%. In some embodiments, the width of the open volume can be greater than the height of the open volume by at most about 1,000%. In some embodiments, the width of the open volume can be greater than the height of the open volume by about 1% to about 2%, about 1% to about 5%, about 1% to about 10%, about 1% to about 20%, about 1% to about 50%, about 1% to about 100%, about 1% to about 200%, about 1% to about 500%, about 1% to about 1,000%, about 2% to about 5%, about 2% to about 10%, about 2% to about 20%, about 2% to about 50%, about 2% to about 100%, about 2% to about 200%, about 2% to about 500%, about 2% to about 1,000%, about 5% to about 10%, about 5% to about 20%, about 5% to about 50%, about 5% to about 100%, about 5% to about 200%, about 5% to about 500%, about 5% to about 1,000%, about 10% to about 20%, about 10% to about 50%, about 10% to about 100%, about 10% to about 200%, about 10% to about 500%, about 10% to about 1,000%, about 20% to about 50%, about 20% to about 100%, about 20% to about 200%, about 20% to about 500%, about 20% to about 1,000%, about 50% to about 100%, about 50% to about 200%, about 50% to about 500%, about 50% to about 1,000%, about 100% to about 200%, about 100% to about 500%, about 100% to about 1,000%, about 200% to about 500%, about 200% to about 1,000%, or about 500% to about 1,000%. In some embodiments, the width of the open volume can be greater than the height of the open volume by about 1%, about 2%, about 5%, about 10%, about 20%, about 50%, about 100%, about 200%, about 500%, or about 1,000%.

In some embodiments, the width of the elongated shaft can be greater than the height of the elongated shaft by about 1% to about 1,000%. In some embodiments, the width of the elongated shaft can be greater than the height of the elongated shaft by at least about 1%. In some embodiments, the width of the elongated shaft can be greater than the height of the elongated shaft by at most about 1,000%. In some embodiments, the width of the elongated shaft can be greater than the height of the elongated shaft by about 1% to about 2%, about 1% to about 5%, about 1% to about 10%, about 1% to about 20%, about 1% to about 50%, about 1% to about 100%, about 1% to about 200%, about 1% to about 500%, about 1% to about 1,000%, about 2% to about 5%, about 2% to about 10%, about 2% to about 20%, about 2% to about 50%, about 2% to about 100%, about 2% to about 200%, about 2% to about 500%, about 2% to about 1,000%, about 5% to about 10%, about 5% to about 20%, about 5% to about 50%, about 5% to about 100%, about 5% to about 200%, about 5% to about 500%, about 5% to about 1,000%, about 10% to about 20%, about 10% to about 50%, about 10% to about 100%, about 10% to about 200%, about 10% to about 500%, about 10% to about 1,000%, about 20% to about 50%, about 20% to about 100%, about 20% to about 200%, about 20% to about 500%, about 20% to about 1,000%, about 50% to about 100%, about 50% to about 200%, about 50% to about 500%, about 50% to about 1,000%, about 100% to about 200%, about 100% to about 500%, about 100% to about 1,000%, about 200% to about 500%, about 200% to about 1,000%, or about 500% to about 1,000%. In some embodiments, the width of the elongated shaft can be greater than the height of the elongated shaft by about 1%, about 2%, about 5%, about 10%, about 20%, about 50%, about 100%, about 200%, about 500%, or about 1,000%.

In some embodiments, the height of the open volume of the first elongate body can be greater than the height of the elongated shaft by about 1% to about 30%. In some embodiments, the height of the open volume of the first elongate body can be greater than the height of the elongated shaft by at least about 1%. In some embodiments, the height of the open volume of the first elongate body can be greater than the height of the elongated shaft by at most about 30%. In some embodiments, the height of the open volume of the first elongate body can be greater than the height of the elongated shaft by about 1% to about 2%, about 1% to about 5%, about 1% to about 10%, about 1% to about 15%, about 1% to about 20%, about 1% to about 25%, about 1% to about 30%, about 2% to about 5%, about 2% to about 10%, about 2% to about 15%, about 2% to about 20%, about 2% to about 25%, about 2% to about 30%, about 5% to about 10%, about 5% to about 15%, about 5% to about 20%, about 5% to about 25%, about 5% to about 30%, about 10% to about 15%, about 10% to about 20%, about 10% to about 25%, about 10% to about 30%, about 15% to about 20%, about 15% to about 25%, about 15% to about 30%, about 20% to about 25%, about 20% to about 30%, or about 25% to about 30%. In some embodiments, the height of the open volume of the first elongate body can be greater than the height of the elongated shaft by about 1%, about 2%, about 5%, about 10%, about 15%, about 20%, about 25%, or about 30%.

In some embodiments, the width of the open volume of the first elongate body can be greater than the width of the elongated shaft by about 1% to about 30%. In some embodiments, the width of the open volume of the first elongate body can be greater than the width of the elongated shaft by at least about 1%. In some embodiments, the width of the open volume of the first elongate body can be greater than the width of the elongated shaft by at most about 30%. In some embodiments, the width of the open volume of the first elongate body can be greater than the width of the elongated shaft by about 1% to about 2%, about 1% to about 5%, about 1% to about 10%, about 1% to about 15%, about 1% to about 20%, about 1% to about 25%, about 1% to about 30%, about 2% to about 5%, about 2% to about 10%, about 2% to about 15%, about 2% to about 20%, about 2% to about 25%, about 2% to about 30%, about 5% to about 10%, about 5% to about 15%, about 5% to about 20%, about 5% to about 25%, about 5% to about 30%, about 10% to about 15%, about 10% to about 20%, about 10 to about 25%, about 10% to about 30%, about 15% to about 20%, about 15% to about 25%, about 15% to about 30%, about 20% to about 25%, about 20% to about 30%, or about 25% to about 30%. In some embodiments, the width of the open volume of the first elongate body can be greater than the width of the elongated shaft by about 1%, about 2%, about 5%, about 10%, about 15%, about 20%, about 25%, or about 30%.

In some embodiments, the width of the open volume of the first elongate body can be greater than a width of the membrane, encapsulation chamber, or reservoir by about 1% to about 40%. In some embodiments, the width of the open volume of the first elongate body can be greater than a width of the membrane, encapsulation chamber, or reservoir by at least about 1%. In some embodiments, the width of the open volume of the first elongate body can be greater than a width of the membrane, encapsulation chamber, or reservoir by at most about 40%. In some embodiments, the width of the open volume of the first elongate body can be greater than a width of the membrane, encapsulation chamber, or reservoir by about 1% to about 2%, about 1% to about 5%, about 1% to about 10%, about 1% to about 15%, about 1% to about 20%, about 1% to about 25%, about 1% to about 30%, about 1% to about 35%, about 1% to about 40%, about 2% to about 5%, about 2% to about 10%, about 2% to about 15%, about 2% to about 20%, about 2% to about 25%, about 2% to about 30%, about 2% to about 35%, about 2% to about 40%, about 5% to about 10%, about 5% to about 15%, about 5% to about 20%, about 5% to about 25%, about 5% to about 30%, about 5% to about 35%, about 5% to about 40%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35%, about 20% to about 40%, about 25% to about 30%, about 25% to about 35%, about 25% to about 40%, about 30% to about 35%, about 30% to about 40%, or about 35% to about 40%. In some embodiments, the width of the open volume of the first elongate body can be greater than a width of the membrane, encapsulation chamber, or reservoir by about 1%, about 2%, about 5%, about 10%, about 15%, about 20%, about 25%, about 30%, about 35%, or about 40%.

In some embodiments, the height of the open volume of the first elongate body can be greater than a height of the membrane, encapsulation chamber, or reservoir by about 1% to about 40%. In some embodiments, the height of the open volume of the first elongate body can be greater than a height of the membrane, encapsulation chamber, or reservoir by at least about 1%. In some embodiments, the height of the open volume of the first elongate body can be greater than a height of the membrane, encapsulation chamber, or reservoir by at most about 40%. In some embodiments, the height of the open volume of the first elongate body can be greater than a height of the membrane, encapsulation chamber, or reservoir by about 1% to about 2%, about 1% to about 5%, about 1% to about 10%, about 1% to about 15%, about 1% to about 20%, about 1% to about 25%, about 1% to about 30%, about 1% to about 35%, about 1% to about 40%, about 2% to about 5%, about 2% to about 10%, about 2% to about 15%, about 2% to about 20%, about 2% to about 25%, about 2% to about 30%, about 2% to about 35%, about 2% to about 40%, about 5% to about 10%, about 5% to about 15%, about 5% to about 20%, about 5% to about 25%, about 5% to about 30%, about 5% to about 35%, about 5% to about 40%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35%, about 20% to about 40%, about 25% to about 30%, about 25% to about 35%, about 25% to about 40%, about 30% to about 35%, about 30% to about 40%, or about 35% to about 40%. In some embodiments, the height of the open volume of the first elongate body can be greater than a height of the membrane, encapsulation chamber, or reservoir by about 1%, about 2%, about 5%, about 10%, about 15%, about 20%, about 25%, about 30%, about 35%, or about 40%.

In some embodiments, the length of the open volume of the first elongate body can be greater than a length of the membrane, encapsulation chamber, or reservoir by about 5% to about 500%. In some embodiments, the length of the open volume of the first elongate body can be greater than a length of the membrane, encapsulation chamber, or reservoir by at least about 5%. In some embodiments, the length of the open volume of the first elongate body can be greater than a length of the membrane, encapsulation chamber, or reservoir by at most about 500%. In some embodiments, the length of the open volume of the first elongate body can be greater than a length of the membrane, encapsulation chamber, or reservoir by about 5% to about 10%, about 5% to about 15%, about 5% to about 25%, about 5% to about 50%, about 5% to about 75%, about 5% to about 100%, about 5% to about 200%, about 5% to about 300%, about 5% to about 400%, about 5% to about 500%, about 10% to about 15%, about 10% to about 25%, about 10% to about 50%, about 10% to about 75%, about 10% to about 100%, about 10% to about 200%, about 10% to about 300%, about 10% to about 400%, about 10% to about 500%, about 15% to about 25%, about 15% to about 50%, about 15% to about 75%, about 15% to about 100%, about 15% to about 200%, about 15% to about 300%, about 15% to about 400%, about 15% to about 500%, about 25% to about 50%, about 25% to about 75%, about 25% to about 100%, about 25% to about 200%, about 25% to about 300%, about 25% to about 400%, about 25% to about 500%, about 50% to about 75%, about 50% to about 100%, about 50% to about 200%, about 50% to about 300%, about 50% to about 400%, about 50% to about 500%, about 75% to about 100%, about 75% to about 200%, about 75% to about 300%, about 75% to about 400%, about 75% to about 500%, about 100% to about 200%, about 100% to about 300%, about 100% to about 400%, about 100% to about 500%, about 200% to about 300%, about 200% to about 400%, about 200% to about 500%, about 300% to about 400%, about 300% to about 500%, or about 400% to about 500%. In some embodiments, the length of the open volume of the first elongate body can be greater than a length of the membrane, encapsulation chamber, or reservoir by about 5%, about 10%, about 15%, about 25%, about 50%, about 75%, about 100%, about 200%, about 300%, about 400%, or about 500%.

In some embodiments, the membrane can comprise about 1 membrane to about 6 membranes. In some embodiments, the membrane can comprise at least about 1 membrane. In some embodiments, the membrane can comprise at most about 6 membranes. In some embodiments, the membrane can comprise about 1 membrane to about 2 membranes, about 1 membrane to about 3 membranes, about 1 membrane to about 4 membranes, about 1 membrane to about 5 membranes, about 1 membrane to about 6 membranes, about 2 membranes to about 3 membranes, about 2 membranes to about 4 membranes, about 2 membranes to about 5 membranes, about 2 membranes to about 6 membranes, about 3 membranes to about 4 membranes, about 3 membranes to about 5 membranes, about 3 membranes to about 6 membranes, about 4 membranes to about 5 membranes, about 4 membranes to about 6 membranes, or about 5 membranes to about 6 membranes. In some embodiments, the membrane can comprise about 1 membrane, about 2 membranes, about 3 membranes, about 4 membranes, about 5 membranes, or about 6 membranes.

In some embodiments, the membrane stand can comprise about 1 clip to about 6 clips. In some embodiments, the membrane stand can comprise at least about 1 clip. In some embodiments, the membrane stand can comprise at most about 6 clips. In some embodiments, the membrane stand can comprise about 1 clip to about 2 clips, about 1 clip to about 3 clips, about 1 clip to about 4 clips, about 1 clip to about 5 clips, about 1 clip to about 6 clips, about 2 clips to about 3 clips, about 2 clips to about 4 clips, about 2 clips to about 5 clips, about 2 clips to about 6 clips, about 3 clips to about 4 clips, about 3 clips to about 5 clips, about 3 clips to about 6 clips, about 4 clips to about 5 clips, about 4 clips to about 6 clips, or about 5 clips to about 6 clips. In some embodiments, the membrane stand can comprise about 1 clip, about 2 clips, about 3 clips, about 4 clips, about 5 clips, or about 6 clips.

In some embodiments, the membrane stand can comprise about 1 ledge to about 6 ledges. In some embodiments, the membrane stand can comprise at least about 1 ledge. In some embodiments, the membrane stand can comprise at most about 6 ledges. In some embodiments, the membrane stand can comprise about 1 ledge to about 2 ledges, about 1 ledge to about 3 ledges, about 1 ledge to about 4 ledges, about 1 ledge to about 5 ledges, about 1 ledge to about 6 ledges, about 2 ledges to about 3 ledges, about 2 ledges to about 4 ledges, about 2 ledges to about 5 ledges, about 2 ledges to about 6 ledges, about 3 ledges to about 4 ledges, about 3 ledges to about 5 ledges, about 3 ledges to about 6 ledges, about 4 ledges to about 5 ledges, about 4 ledges to about 6 ledges, or about 5 ledges to about 6 ledges. In some embodiments, the membrane stand can comprise about 1 ledge, about 2 ledges, about 3 ledges, about 4 ledges, about 5 ledges, or about 6 ledges.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which.

DETAILED DESCRIPTION OF THE INVENTION

Figure 1:
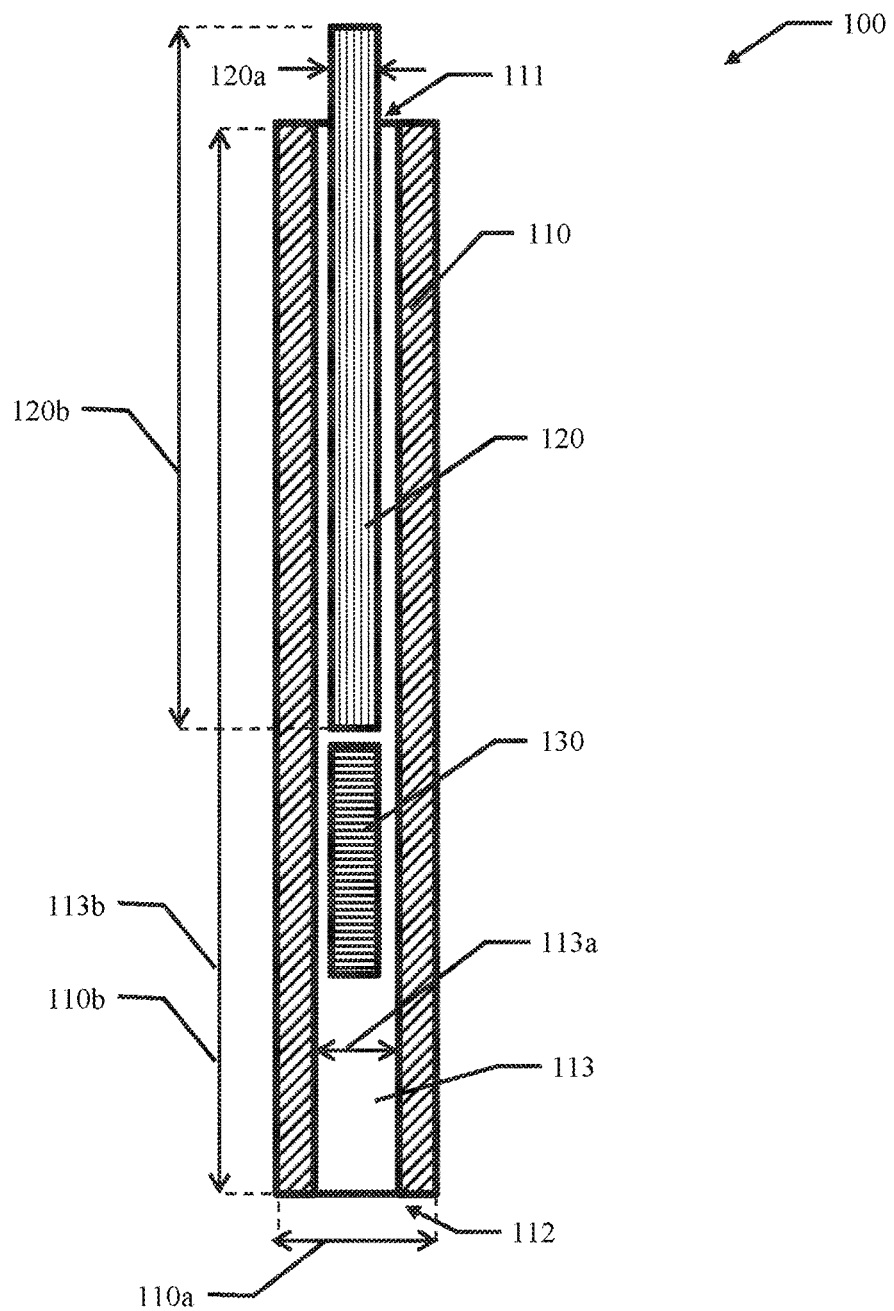
FIG. 1 is a side cross-sectioned view of a non-limiting exemplary membrane implantation device, in accordance with some embodiments.

Provided herein are devices, systems, and methods for implanting a membrane, encapsulation chamber, or reservoir into a patient. The devices, systems, and methods herein are configured to subcutaneously insert a membrane, encapsulation chamber, or reservoir into a precise and accurate location within the subject. Each of the membrane, encapsulation chamber, or reservoir can allow for the diffusion of one or more therapeutic protein or compound from within the membrane into the subject. In some embodiments, the devices, systems, and methods herein can be configured to remove a membrane, encapsulation chamber, or reservoir that was previously subcutaneously inserted into a subject. As some implantation membranes, encapsulation chambers, and reservoirs are non-rigid, the aspects of the disclosure herein can prevent damage or deformation of the non-rigid membrane, encapsulation chamber, or reservoir during insertion or removal. In some embodiments, membranes, encapsulation chambers, or reservoirs can comprise encapsulated cells or therapeutics, wherein the cells can be insulin producing cells.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "generally" refers to a quality that is near the stated quality by 10%, 5%, or 1%, including increments therein.

As used herein, the term "aperture" refers to a rigid opening, gap, inlet, or outlet.

As used herein, the term "membrane" refers to a substrate for cell growth or storage. In some embodiments, at least one or more cell within the membrane can be capable of becoming vascularized. In some embodiments, at least one or more cell within the membrane can be capable of becoming vascularized and integrated with in the subject's systemic vasculature. In some embodiments, the membrane can be shielded from the subject's immune system such that the subject does not require one or more immuno-suppressive drug. In some embodiments, the membrane can be biodegradable. In some embodiments, the membrane can allow for diffusion of a therapeutic agent, e.g., a protein or compound made by one or more cell within the membrane, out of the membrane.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure.

Figure 2:
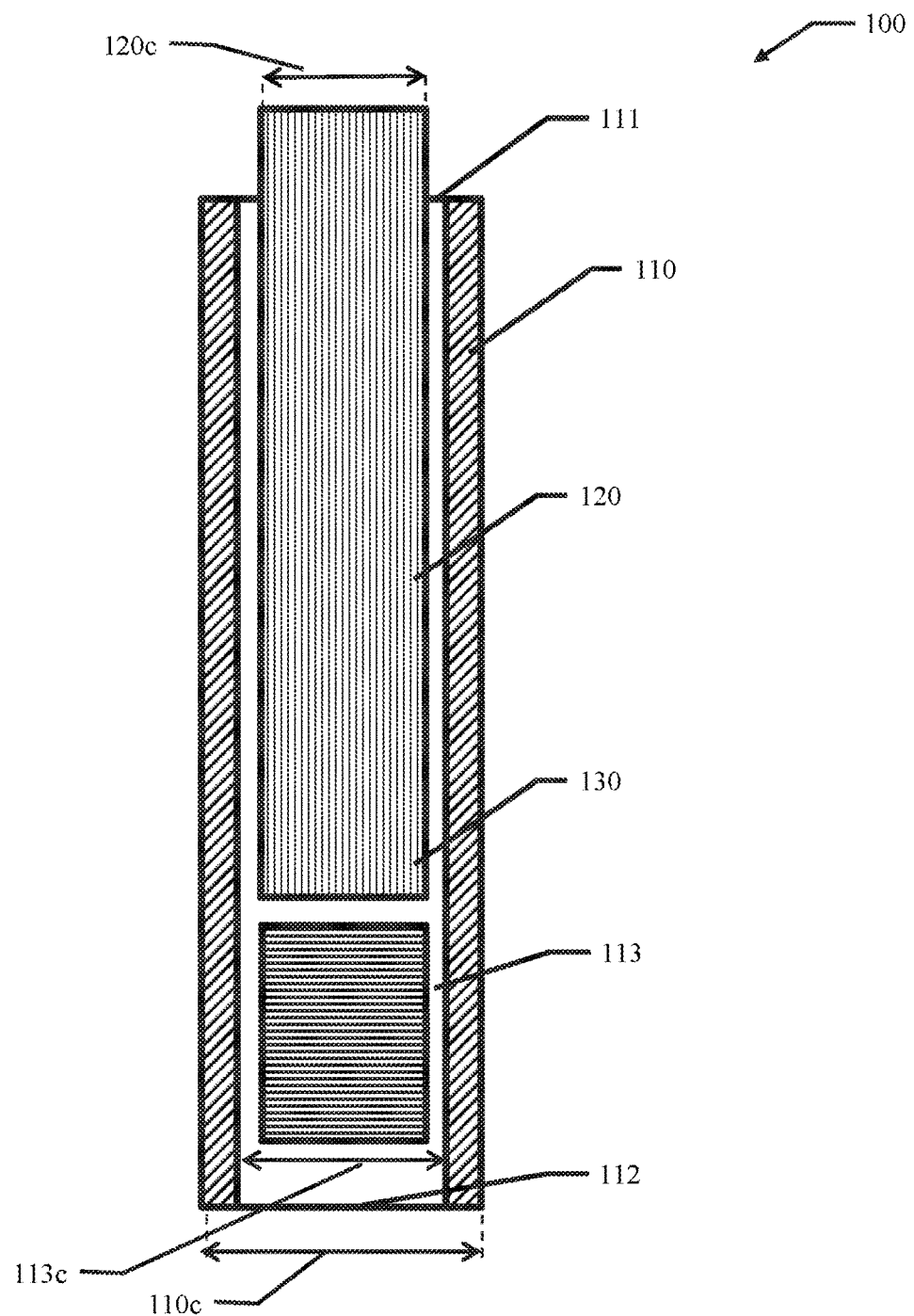
FIG. 2 is a top cross-sectioned view of a non-limiting exemplary membrane implantation device, in accordance with some embodiments.

Provided herein, per FIGS. 1-10 are implantation devices for delivering cells, therapeutics, or generally particles of interest to a subject. As shown in FIGS. 1-2, the implantation device 100 described herein can comprise a first body 110 and a second body 120. Each of the first and second bodies can or can not comprise elongate structures. Accordingly, while elongate bodies are primarily described herein, it is to be understood that the first and/or second bodies can not be elongate bodies. In embodiments described herein, the first body 110 can comprise a proximal portion, a distal portion, and an open volume 113. The open volume can be configured to hold cells, therapeutics, or particles of interest. In some instances, the cells, therapeutics, or particles of interest can be on a membrane 130, or be encapsulated within a membrane, and the implantation device can also be referred to herein as a membrane implantation device. However, it is to be understood that the cells, therapeutics, or particles of interest can be delivered directly, or within other outer shells or coatings other than a membrane via the implantation devices described herein. In some instances, the open volume 113 of the first body can lead to an opening 112 at the distal portion. As shown, the proximal portion of the open volume 113 can have a proximal aperture 111 and the distal portion of the open volume 113 can have a distal aperture 112. However, it is to be understood that the first body does not necessarily need to have both a proximal and distal aperture. For example, the first body can have a single aperture (e.g., at a distal or proximal end) or can have a plurality of apertures, for example, two, three, four, five, six, or seven apertures.

The membrane implantation device 100 herein can be configured such that at least the distal portion of the second elongate body 110 is sized to fit within the open volume 113 of the first elongate body 110. Further, in some cases, the membrane implantation device 100 herein can be configured such that the second elongate body 120 is configured to translate relative to the first elongate body 110. Additionally, at least one of the open volume 113, the proximal aperture 111, and the distal aperture 112 are configured to receive a membrane 130. Further, the second elongate body 120 is configured to prevent translation of the membrane 130 in a direction from the proximal aperture to the 112 proximal aperture 111. In some embodiments, the proximal portion of the first elongate body 110 can be proximally located relative to the proximal portion of the second elongate body 120.

Per FIGS. 1-2 the open volume 113 and the second elongate body 120 of the membrane implantation device 100 have a normal cross-sectional shape comprising a rectangle. In some embodiments, at least one of the open volume 113 and the second elongate body 120 can have a normal cross-sectional shape comprising a circle, an oval, an ellipse, a triangle, a square, a regular polygon, an irregular polygon, or any combination thereof. In some embodiments, the open volume 113 and the second elongate body 120 of the membrane implantation device 100 can be generally straight in a direction from the proximal portion to the distal portion. The first elongate body is generally flat in some embodiments. Further, in some cases, the centroids of the cross sections of least one of the open volume 113 and the second elongate body 120 in a direction from the proximal portion to the distal portion form a line or a continuous curve, or both. In some embodiments, the second elongate body 120 can comprise a cross sectional area generally equal to a cross sectional area of the open volume 113. In some embodiments, the first elongate body 110 can comprise a generally uniform width and height throughout. Further, the open volume 113 can comprise a width generally equal to a width of the opening 112, and in some embodiments, the open volume 113 can comprise a uniform width.

In some embodiments, at least one of the first elongate body 110 and the second elongate body 120 can further comprise a bearing. Additionally, at least one of the first elongate body 110 and the second elongate body 120 can comprise one or more permanently adjoined parts. At least one of the first elongate body 110 and the second elongate body 120 per any embodiment herein are composed of metal, plastic, carbon fiber, fiberglass, wood, ceramic, or any combination thereof. In some embodiments, at least one of the first elongate body 110 and the second elongate body 120 can be composed of titanium, aluminum, stainless steel, or any combination thereof.

In some embodiments, the membrane implantation device 100 can comprise an average thickness equal to or less than about 1 cm, or equal to or less than about 0.5 cm. The membrane implantation device 100 in some embodiments can comprise an average width equal to or less than about 5 cm. Additionally, the membrane implantation device 100 in some embodiments, can comprise a length equal to or less than about 30 cm. In some embodiments, a ratio of a width of the first elongate body 110 to a height of the first elongate body 110 can be equal to or greater than about 5:1. In some embodiments, a width of the membrane can be equal to or greater than 70% of a width of the open volume. Further, the membrane implantation device 100 can comprise a volume equal to or less than about 40 cm^3. In some embodiments, a ratio of a width of the first elongate body 110 to a height of the first elongate body 110 can be equal to or greater than about 5:1. In some embodiments, the opening 112 can comprise a dimension equal to or greater than about 1 cm.

In some embodiments, per FIGS. 1 and 2, the first elongate body 110 can be configured with at least one of: a width 110c of about 0.75 cm to about 3 cm; a height 110a of about 0.05 cm to about 3 cm; and a length 110b of about 5 cm to about 30 cm. In some embodiments, at least one of the proximal portion and the distal portion of the first elongate body 110 can have a height 110a of about 0.05 cm to about 3 cm. At least one of the height 110a and the width 110c of the first elongate body 110, per some embodiments, can be configured to form a structure of the first elongate body 110 with a sufficient thickness and rigidity. In some embodiments, the device can comprise an average thickness equal to or less than about 1 cm, or equal to or less than about 0.5 cm. Further, in some embodiments, at least one of the height 110a and the width 110c of the first elongate body 110 can be minimized to decrease the size of the required incision for insertion. Finally, in some embodiments, the length 110b of the first elongate body 110 can be configured to be at least the sum of the length 120b of the second elongate body 120 and the length 130b of the membrane 130.

Per FIG. 1, the height 110a of the first elongate body 110 is measured as a normal distance between a top outer side of the first elongate body 110 and an opposing bottom outer side of the first elongate body 110. In some embodiments, the height 110a of the first elongate body 110 can be measured as a minimum or a maximum normal distance between a top outer side of the first elongate body 110 and an opposing bottom outer side of the first elongate body 110. Alternatively, in some embodiments, the height 110a of the first elongate body 110 can be measured as a minimum or a maximum distance between a top outer side of the first elongate body 110 and an opposing bottom outer side of the first elongate body 110. Alternatively, in some embodiments, the height 110a of the first elongate body 110 can be measured as a normal distance between the proximal aperture 111 and the distal aperture 112 of the first elongate body 110. In some embodiments, the height 110a of the first elongate body 110 can be measured, as a minimum or maximum normal distance between the proximal aperture 111 and the distal aperture 112 of the first elongate body 110. Finally, in some embodiments, the height 110a of the first elongate body 110 can be measured, as a minimum or maximum distance between the proximal aperture 111 and the distal aperture 112 of the first elongate body 110.

Per FIG. 2, the width 110a of the first elongate body 110 is measured as a normal distance between a left outer side of the first elongate body 110 and an opposing right outer side of the first elongate body 110. In some embodiments, the width 110a of the first elongate body 110 can be measured as a minimum or a maximum normal distance between a left outer side of the first elongate body 110 and an opposing right outer side of the first elongate body 110. Alternatively, in some embodiments, the width 110a of the first elongate body 110 can be measured as a minimum or a maximum distance between a left outer side of the first elongate body 110 and an opposing right outer side of the first elongate body 110.

In some embodiments, the open volume 113 can be configured with at least one of: a height 113a of about 0.01 cm to about 5 cm; a length 113b of about 5 cm to about 30 cm; and a width 113c of about 0.2 cm to about 10 cm. In some embodiments, the dimensions of the open volume 113 including at least one of the height 113a and the width 113c of the open volume 113 can be configured to accept and slideably couple with the second elongate body 120 and the membrane 130 without jamming. In some embodiments, the length 113b of the open volume 113 can be configured to be at least the sum of the length 120b of the second elongate body 120 and the length 130b of the membrane 130.

Per FIG. 1, the height 113a of the open volume 113 is measured as a normal distance between a top outer side of the open volume 113 and an opposing bottom outer side of the open volume 113. In some embodiments, the height 113a of the open volume 113 can be measured as a minimum or a maximum normal distance between a top outer side of the open volume 113 and an opposing bottom outer side of the open volume 113. Alternatively, in some embodiments, the height 113a of the open volume 113 can be measured as a minimum or a maximum distance between a top outer side of the open volume 113 and an opposing bottom outer side of the open volume 113.

Per FIG. 1, the length 113a of the open volume 113 can be measured as a normal distance between the proximal aperture 111 and the distal aperture 112 of the open volume 113. In some embodiments, the length 113a of the open volume 113 can be measured, as a minimum or maximum normal distance between the proximal aperture 111 and the distal aperture 112 of the open volume 113. Alternatively, in some embodiments, the length 113a of the open volume 113 can be measured, as a minimum or maximum distance between the proximal aperture 111 and the distal aperture 112 of the open volume 113.

Per FIG. 2, the width 113a of the open volume 113 can be measured as a normal distance between a left outer side of the open volume 113 and an opposing right outer side of the open volume 113. In some embodiments, the width 113a of the open volume 113 can be measured as a minimum or a maximum normal distance between a left outer side of the open volume 113 and an opposing right outer side of the open volume 113. Alternatively, in some embodiments, the width 113a of the open volume 113 can be measured as a minimum or a maximum distance between a left outer side of the open volume 113 and an opposing right outer side of the open volume 113.

In some embodiments, the second elongate body 120 can have a height 120a of about 0.01 cm to about 5 cm. In some embodiments, the second elongate body 120 can have a length 120b of about 5 cm to about 30 cm. In some embodiments, the second elongate body 120 can have a width 120c of about 0.2 cm to about 10 cm. In some embodiments, at least one of the height 120a and the width 120c of the second elongate body 120 can be configured to form a structure of the second elongate body 120 with a sufficient thickness and rigidity to advance the membrane 130. In some embodiments, at least one of the height 120a and the width 120c of the second elongate body 120 can be equal to a height and a width of the membrane 130, respectively. In some embodiments, at least one of the height 120a and the width 120c of the second elongate body 120 can be greater or less than the height and the width of the membrane 130, respectively.

Per FIG. 1, the height 120a of the second elongate body 120 can be measured as a normal distance between a top outer side of the second elongate body 120 and an opposing bottom outer side of the second elongate body 120. In some embodiments, the height 120a of the second elongate body 120 can be measured as a minimum or a maximum normal distance between a top outer side of the second elongate body 120 and an opposing bottom outer side of the second elongate body 120. Alternatively, in some embodiments, the height 120a of the second elongate body 120 can be measured as a minimum or a maximum distance between a top outer side of the second elongate body 120 and an opposing bottom outer side of the second elongate body 120.

Per FIG. 1, the height 120a of the second elongate body 120 can be measured as a normal distance between the proximal aperture 111 and the distal aperture 112 of the second elongate body 120. In some embodiments, the height 120a of the second elongate body 120 can be measured, as a minimum or maximum normal distance between the proximal aperture 111 and the distal aperture 112 of the second elongate body 120. Alternatively, in some embodiments, the height 120a of the second elongate body 120 can be measured, as a minimum or maximum distance between the proximal aperture 111 and the distal aperture 112 of the second elongate body 120.

Per FIG. 2, the width 120a of the second elongate body 120 can be measured as a normal distance between a left outer side of the second elongate body 120 and an opposing right outer side of the second elongate body 120. In some embodiments, the width 120a of the second elongate body 120 can be measured as a minimum or a maximum normal distance between a left outer side of the second elongate body 120 and an opposing right outer side of the second elongate body 120. Alternatively, in some embodiments, the width 120a of the second elongate body 120 can be measured as a minimum or a maximum distance between a left outer side of the second elongate body 120 and an opposing right outer side of the second elongate body 120.

In some embodiments, the width 110c of the first elongate body 110 can be greater than the width 113c of the open volume 113 by about 1% to about 50%. In some embodiments, the height 110a of the first elongate body 110 can be greater than the width 113c of the open volume 113 by about 1% to about 50%. In some embodiments, the length 110b of the first elongate body 110 can be greater than the length 113b of the open volume 113 by at most about 50%. In some embodiments, the width 110c of the first elongate body 110 can be greater than the height 110a of the first elongate body 110 by about 1% to about 5000%. In some embodiments, the width 113c of the open volume 113 can be greater than the height 113a of the open volume 113 by about 1% to about 5000%. In some embodiments, the height 113a of the open volume 113 of the first elongate body 110 can be greater than the height of the second elongate body 120 by about 1% to about 30%. In some embodiments, the width of the open volume 113 of the first elongate body 110 can be greater than the width of the second elongate body 120 by about 1% to about 30%. In some embodiments, the width of the second elongate body 120 can be greater than the height of the second elongate body 120 by about 1% to about 5000%. In some embodiments, a ratio between the height 113a of the open volume 113 or the width 113c of the open volume 113, and the height 120a of the second elongate body 120 or the width 120c of the second elongate body 120 can be configured to enable sliding contact, while prevent jamming, between the second elongate body 120 within the open volume 120. In some embodiments, the opening 112 can comprise a dimension equal to or greater than about 1 cm. In some embodiments, the opening can comprise a width equal to or greater than about 0.5 cm, 1 cm, 1.5 cm, 2 cm, 2.5 cm, 3 cm. 3.5 cm, 4 cm, 4.5 cm, 5 cm, 6 cm, 7 cm, 8 cm, 9 cm, 10 cm, or any value there between. In some embodiments, the opening can comprise a generally flat shape. In some embodiments, the opening can comprise a width generally equal to a width of the open volume. In some embodiments, the opening can comprise a curvature. For example, the opening can be curved, e.g., concave in or concave out. In some embodiments, a second body can have a curvature. In some embodiments, the curvature of the second body can be complementary to a curvature of the opening. For example, if the opening has a concave out curvature, the second body can have a concave in curvature. In some embodiments, the second body can partially advance outside the opening of the first body.

Provided herein, per, for example, FIGS. 3-7 is a first exemplary membrane implantation device 300 for delivering cells or therapeutics to a subject comprising a first elongate body 310 and a second elongate body 320. In some embodiments, the first elongate body 310 can comprise a proximal portion, a distal portion, and an open volume configured to hold the cells or therapeutics on a membrane 330, wherein the open volume leads to an opening at the distal portion. As shown, the distal portion of the open volume can have a distal aperture 311 and the proximal portion of the open volume can have a proximal aperture.

Per FIGS. 3-7 the open volume and the second elongate body 320 can have a normal cross-sectional shape comprising a rectangle. In some embodiments, at least one of the open volume 313 and the second elongate body 320 can have a normal cross-sectional shape comprising a circle, an oval, an ellipse, a triangle, a square, a regular polygon, an irregular polygon, or any combination thereof. In some embodiments, the open volume and the second elongate body 320 can be generally straight in a direction from the proximal portion to the distal portion. In some embodiments, the first elongate body can be generally flat in some embodiments. Further, in some embodiments, the centroids of the cross sections of least one of the open volume and the second elongate body 320 in a direction from the proximal portion to the distal portion can form a line or a continuous curve, or both. In some embodiments, the second elongate body 320 can comprise a cross sectional area generally equal to a cross sectional area of the open volume. In some embodiments, the first elongate body 310 can comprise a generally uniform width and height throughout. Further, in some embodiments, the open volume can comprise a width generally equal to a width of the opening 312 and optionally, the open volume comprises a uniform width.

Figure 4:
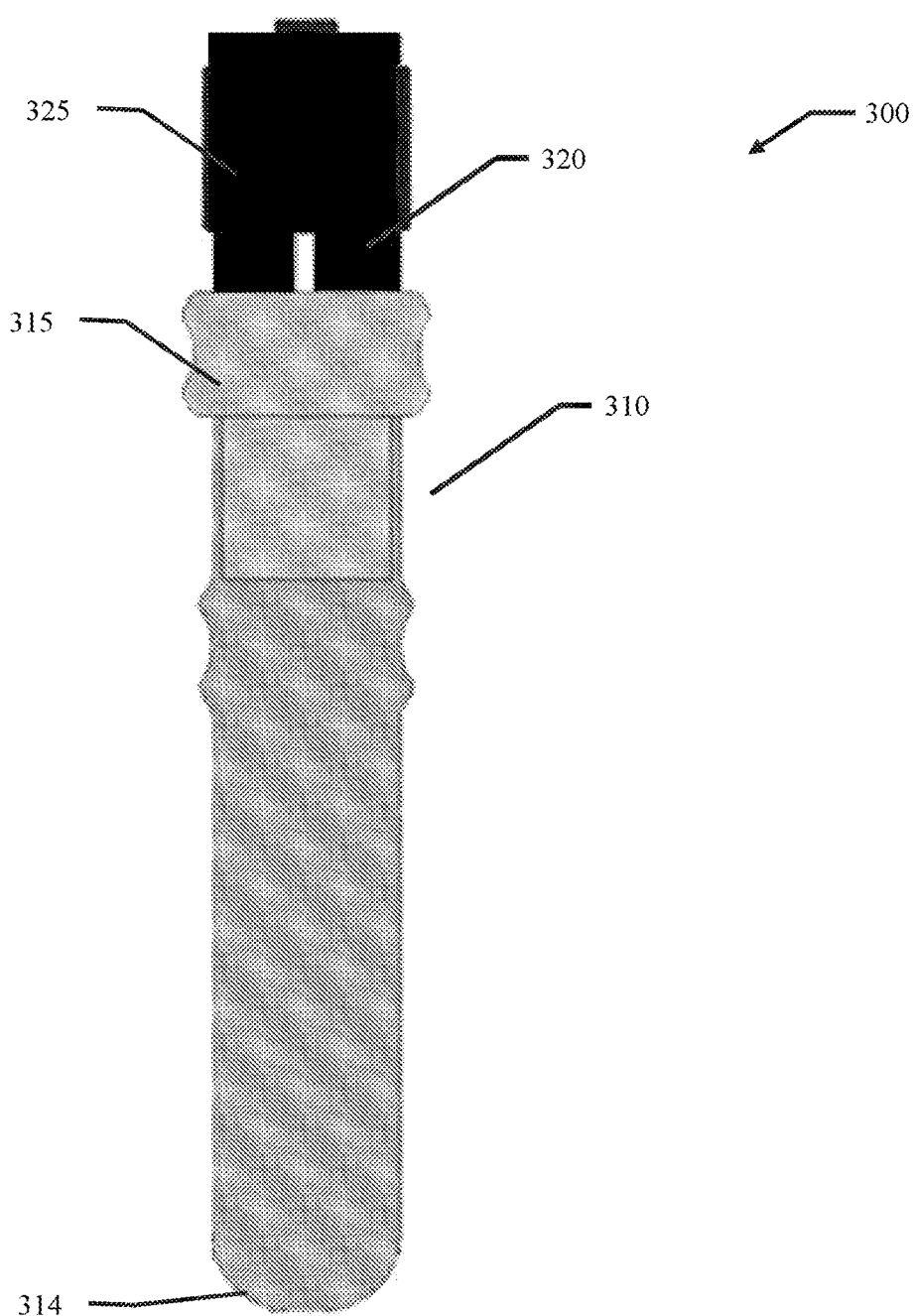
FIG. 4 is a top view of a non-limiting exemplary first membrane implantation device, in accordance with some embodiments.

Per FIG. 4, the distal portion of the first elongate body 310 of the first exemplary device 300 can comprise a fillet 314. In some embodiments, the distal portion of the first elongate body 310 can comprise a chamfer. In some embodiments, per FIG. 4, the first elongate body 310 can comprise a first elongate body grip 315. In some embodiments, the second elongate body 320 can comprise a second elongate body grip 325. Per FIG. 6, in some embodiments, the distal portion of the second elongate body 320 of the first exemplary device 300 can comprise a divot 324 along the width of the second elongate body 320. As shown, the divot, in some embodiments, can be centered along the width of the second elongate body 320 and comprises a concave radius.

Figure 3:
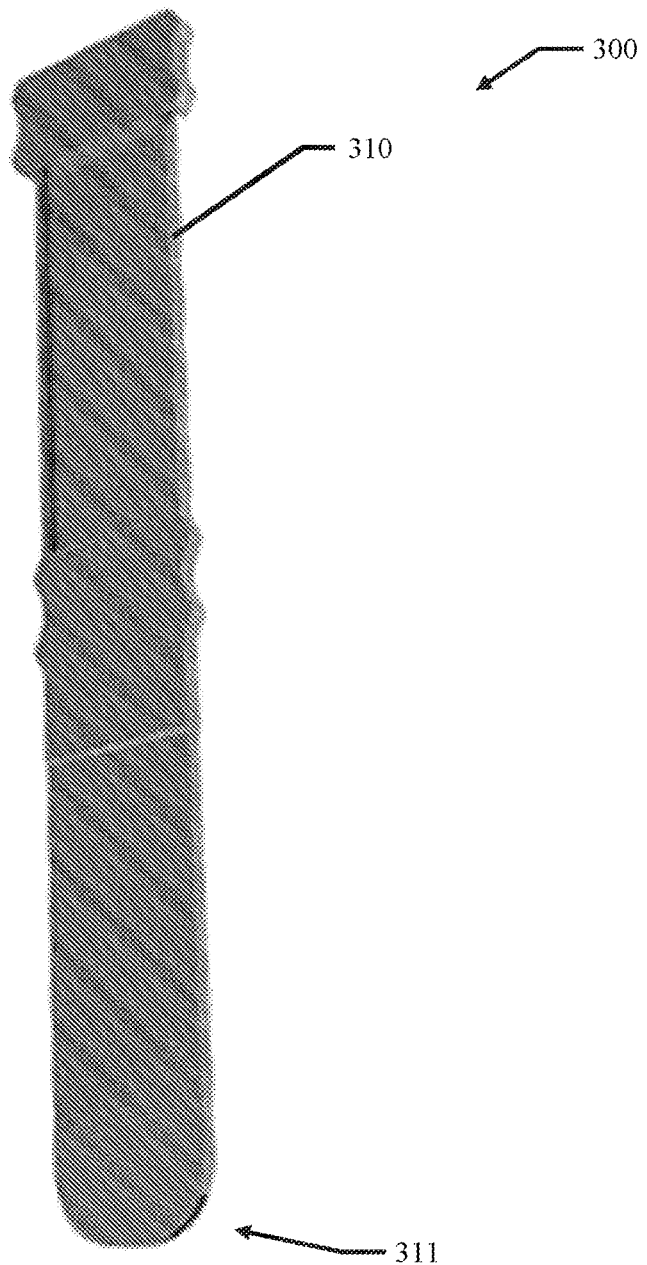
FIG. 3 is a top perspective view of a non-limiting exemplary first membrane implantation device, in accordance with some embodiments.
Figure 5:
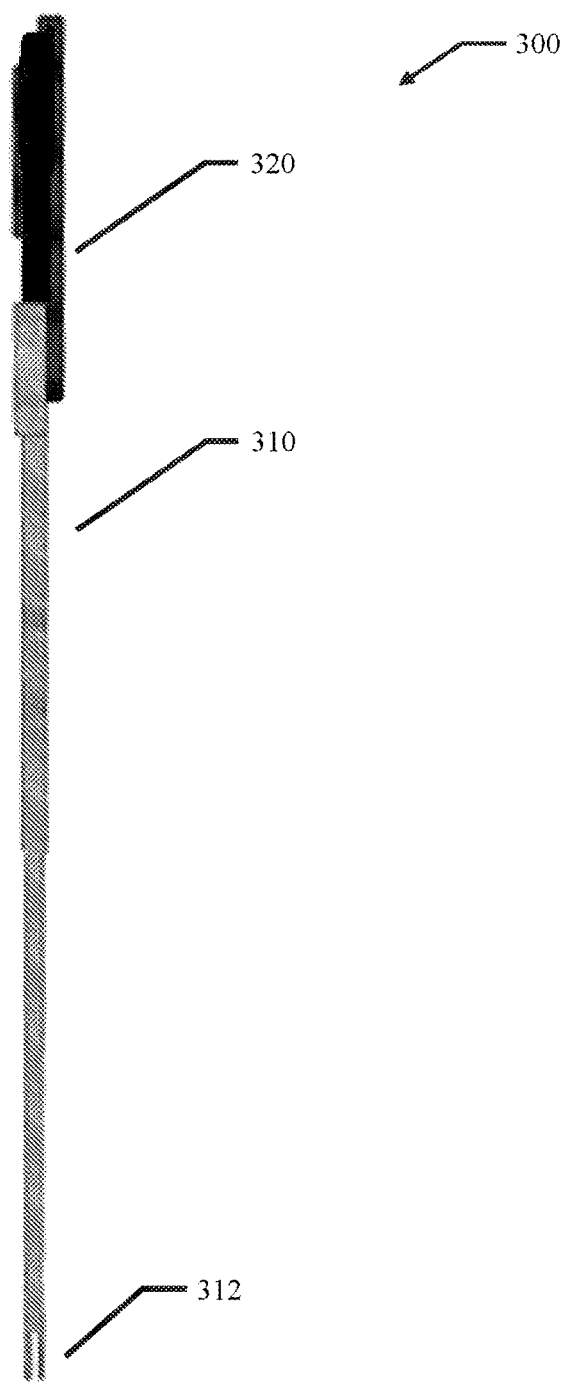
FIG. 5 is a side view of a non-limiting exemplary first membrane implantation device, in accordance with some embodiments.
Figure 6:
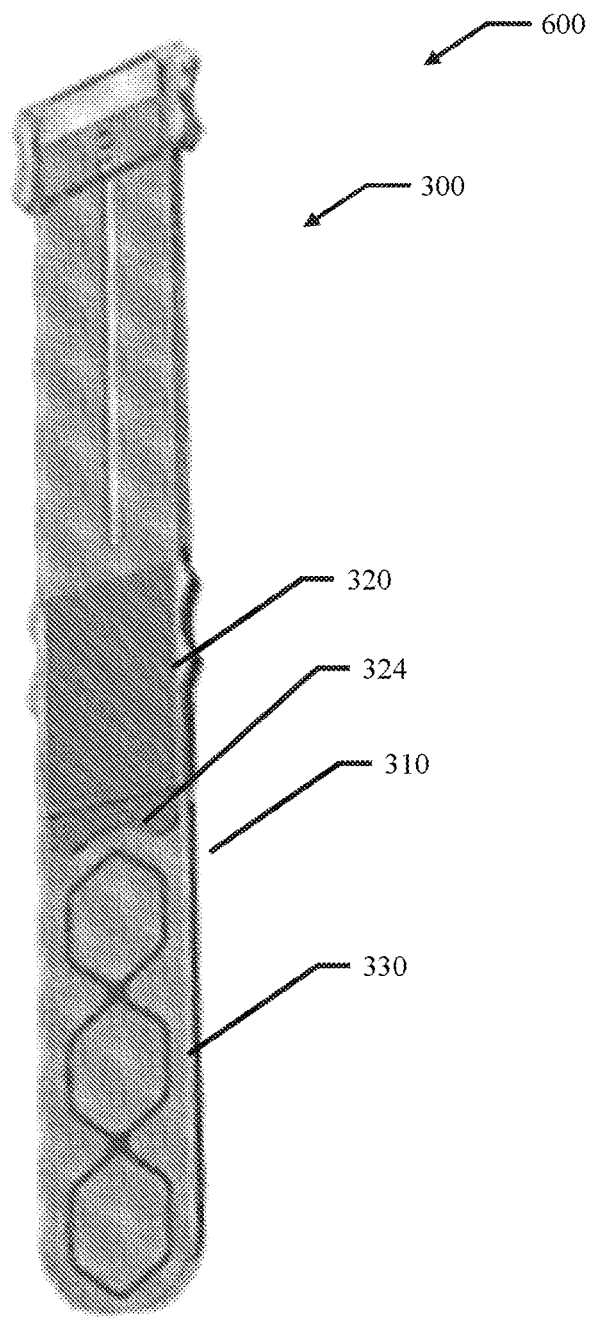
FIG. 6 is a top perspective view of a non-limiting exemplary first membrane implantation device containing a non-limiting exemplary membrane, in accordance with some embodiments.
Figure 7:
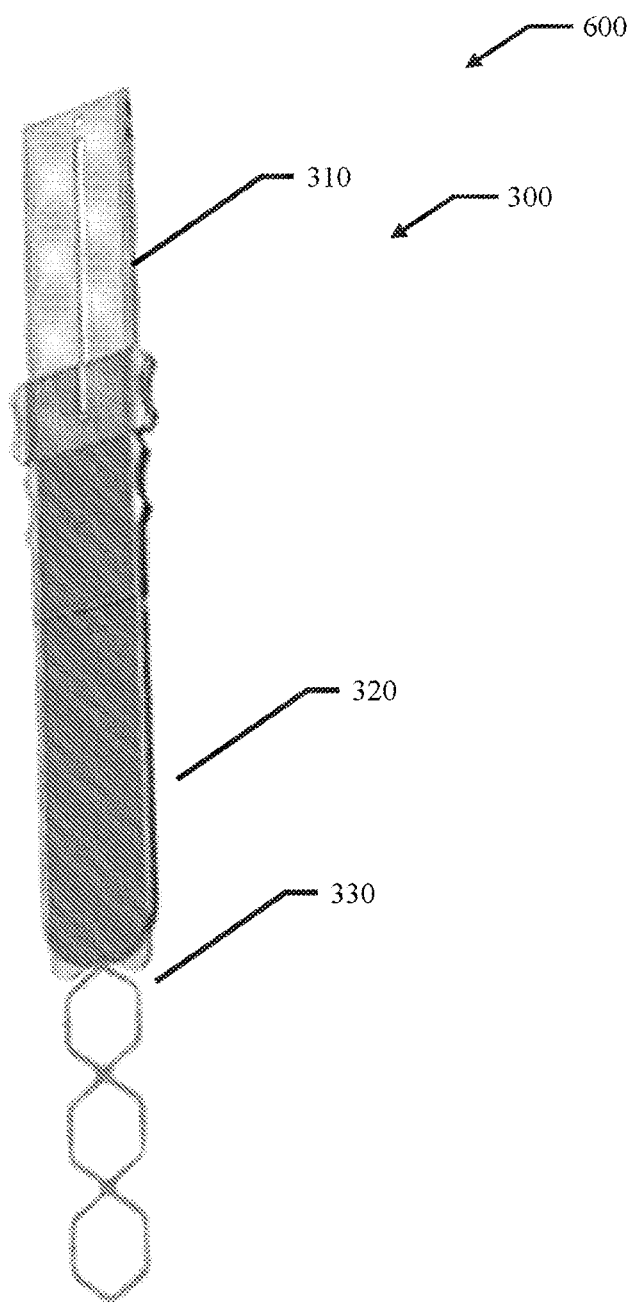
FIG. 7 is a top perspective view of a non-limiting exemplary first membrane implantation device releasing a non-limiting exemplary membrane, in accordance with some embodiments.

Further provided herein, per FIGS. 6 and 7, is an exemplary first membrane implantation system 600 for delivering cells or therapeutics to a subject, the system 600 comprising: a membrane 330 configured to hold the cells or therapeutics; the first elongate body 310 of FIGS. 3-5 comprising an open volume configured to hold the membrane 330 and; the second elongate body 320 of FIGS. 3-5 sized to fit within the open volume of the first elongate body 310, and move relative to the first elongate body 310. Further, the second elongate body 320 per some embodiments can be configured to prevent translation of the membrane 330 within the open volume. As shown, the distal portion of the open volume can have a distal aperture 312.

In some embodiments, the first membrane implantation system 600 can comprise an average thickness equal to or less than about 1 cm, or equal to or less than about 0.5 cm. The implantation system 100 in some embodiments can comprise an average width equal to or less than about 5 cm. Additionally, the first membrane implantation system 600 in some embodiments, can comprise a length equal to or less than about 30 cm. Further, the membrane implantation system 100 in some embodiments, can comprise a volume equal to or less than about 40 cm^3.

Figure 8:
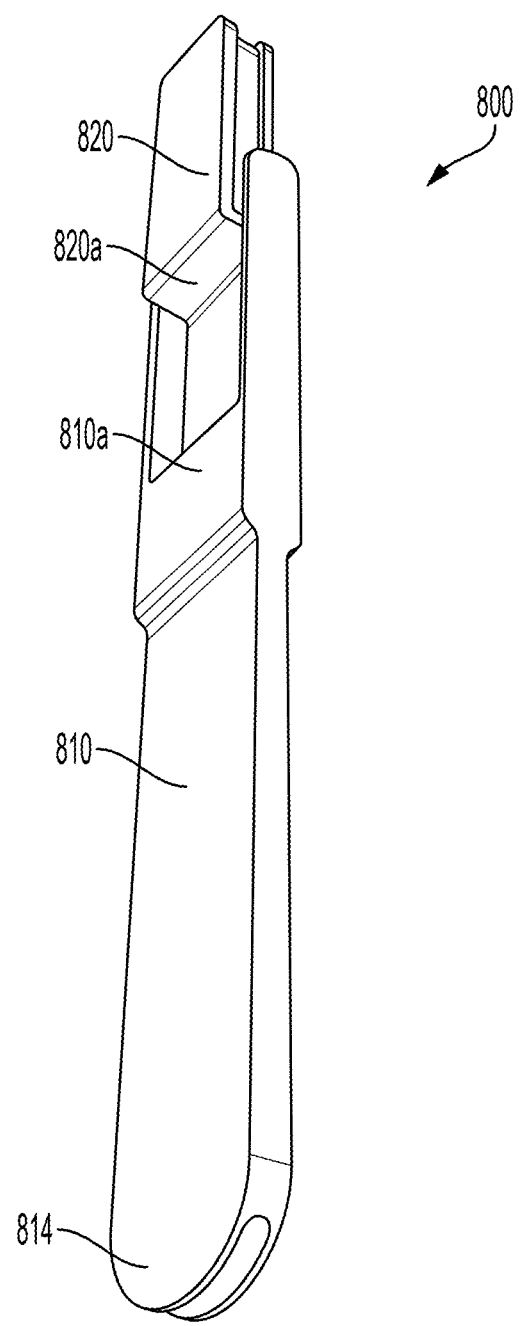
FIG. 8 is a top perspective view of a non-limiting exemplary second membrane implantation device, in accordance with some embodiments.
Figure 9:
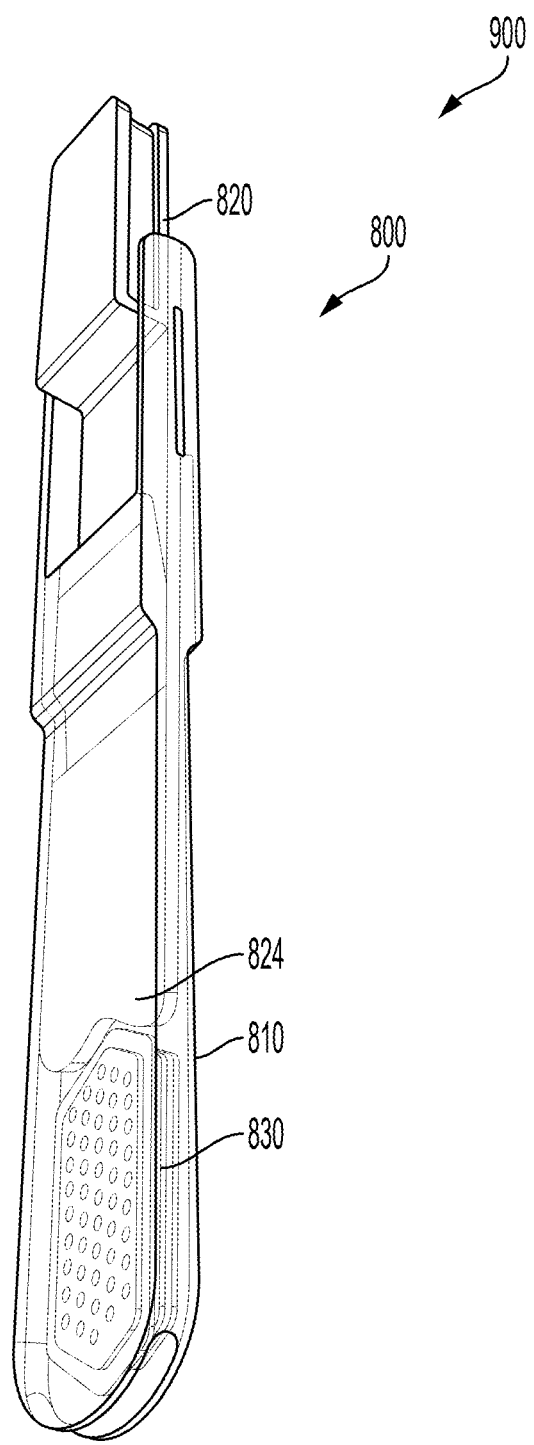
FIG. 9 is a top perspective view of a non-limiting exemplary second membrane implantation device containing a non-limiting exemplary membrane, in accordance with some embodiments.
Figure 10:
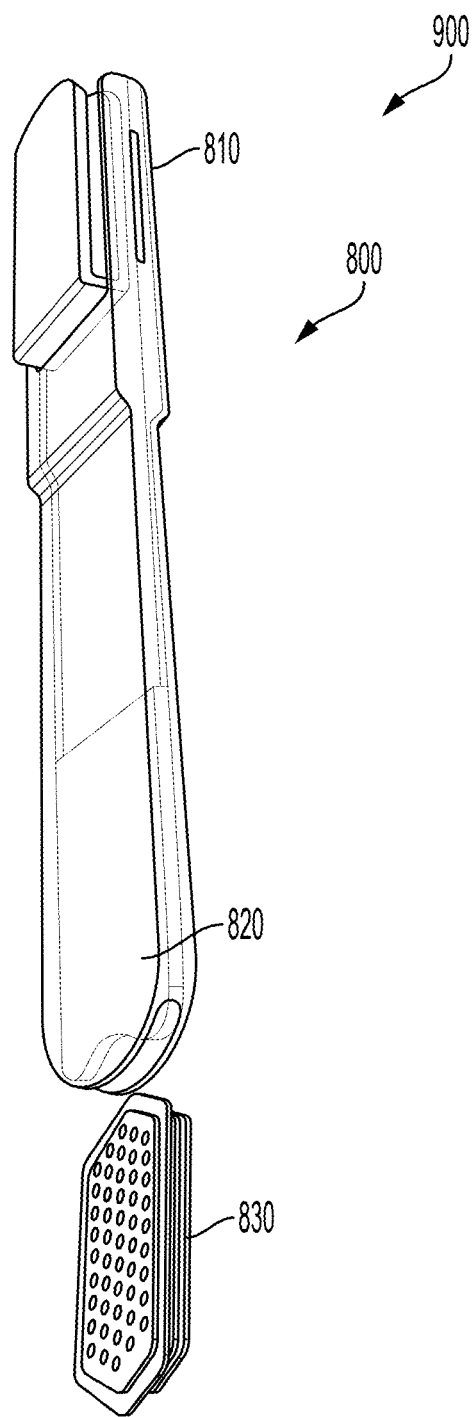
FIG. 10 is a top perspective view of a non-limiting exemplary second membrane implantation device releasing a non-limiting exemplary membrane, in accordance with some embodiments.

Provided herein, per, for example, FIGS. 8-10 is a second exemplary membrane implantation device 600 for delivering cells or therapeutics to a subject comprising a first elongate body 610 and a second elongate body 620. In some embodiments, the first elongate body 610 can comprise a proximal portion, a distal portion, and an open volume configured to hold the cells or therapeutics on a membrane 630, wherein the open volume leads to an opening at the distal portion. As shown, the distal portion of the open volume can have a distal aperture 611 and the proximal portion of the open volume can have a proximal aperture.

Per FIGS. 8-10 the open volume and the second elongate body 820 can have a normal cross-sectional shape comprising a rectangle. In some embodiments, at least one of the open volume 813 and the second elongate body 820 can have a normal cross-sectional shape comprising a circle, an oval, an ellipse, a triangle, a square, a regular polygon, an irregular polygon, or any combination thereof. In some embodiments, the open volume and the second elongate body 820 can be generally straight in a direction from the proximal portion to the distal portion. The first elongate body can be generally flat in some embodiments. Further, in some embodiments, the centroids of the cross sections of least one of the open volume and the second elongate body 820 in a direction from the proximal portion to the distal portion can form a line or a continuous curve, or both. In some embodiments, the second elongate body 820 can comprise a cross sectional area generally equal to a cross sectional area of the open volume. In some embodiments, the first elongate body 810 can comprise a generally uniform width and height throughout. Further, in some embodiments, the open volume can comprise a width generally equal to a width of the opening 812, and in some embodiments, the open volume can comprise a uniform width.

Per FIG. 8, the distal portion of the first elongate body 810 of the first exemplary device 800 can comprise a fillet 814. Alternatively, in some embodiments, the distal portion of the first elongate body 810 can comprise a chamfer. In some embodiments, per FIG. 8, the first elongate body 810 can comprise a first stop 810a and the second elongate body 820 comprises a second stop 820a, wherein the first stop 810a and the second stop 820a can be configured to maintain the second elongate body 820 within the open volume of the first elongate body 810. Per FIG. 9, in some embodiments, the distal portion of the second elongate body 820 of the first exemplary device 800 can comprise a divot 824 along the width of the second elongate body 820. As shown, the divot, in some embodiments, can be centered along the width of the second elongate body 820 and comprises a concave radius.

Further provided herein, per FIGS. 9 and 10, is an exemplary second system 900 for delivering cells or therapeutics to a subject, the system 900 comprising: a membrane 830 configured to hold the cells or therapeutics; the first elongate body 810 of FIG. 8 comprising an open volume configured to hold the membrane 830 and; the second elongate body 820 of FIG. 8 sized to fit within the open volume of the first elongate body 810, and move relative to the first elongate body 810. Further, the second elongate body 820 per some embodiments can be configured to prevent translation of the membrane 830 within the open volume.

In some embodiments, the second membrane implantation system 600 can comprise an average thickness equal to or less than about 1 cm, or equal to or less than about 0.5 cm. The membrane implantation system 800 in some embodiments can comprise an average width equal to or less than about 5 cm. Additionally, the second membrane implantation system 800 in some embodiments, can comprise a length equal to or less than about 30 cm. Further, in some embodiments, the membrane implantation system 800 can comprise a volume equal to or less than about 40 cm^3.

Figure 11:
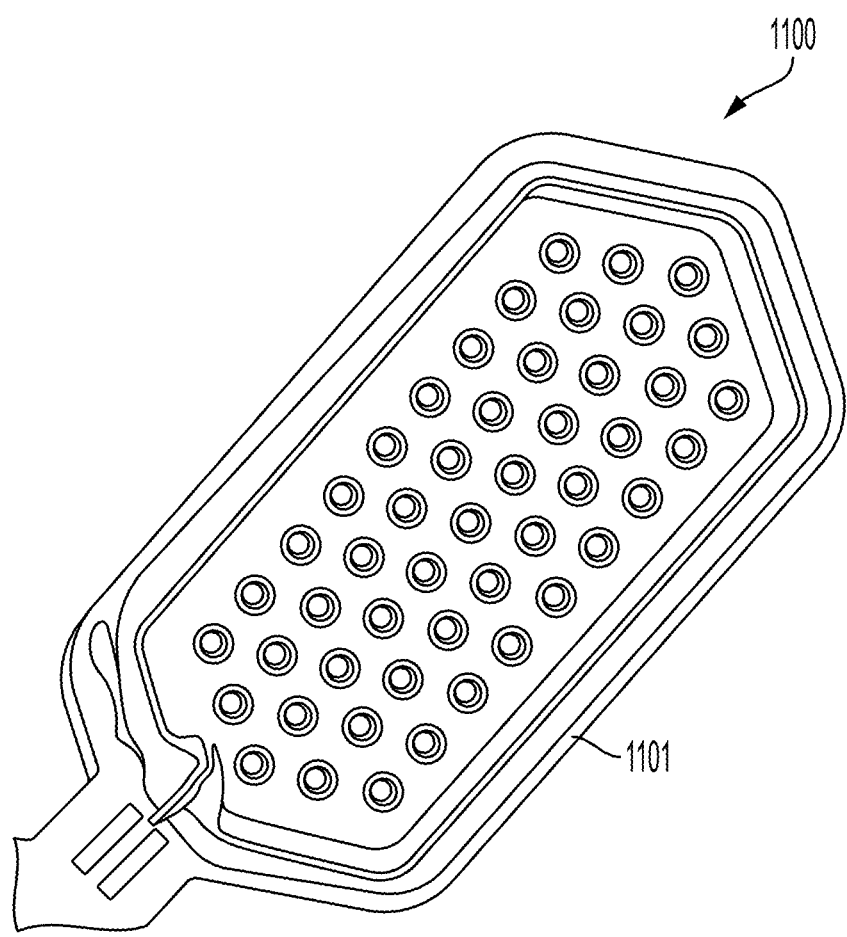
FIG. 11 is a top view of a first non-limiting exemplary membrane, in accordance with some embodiments.
Figure 12:
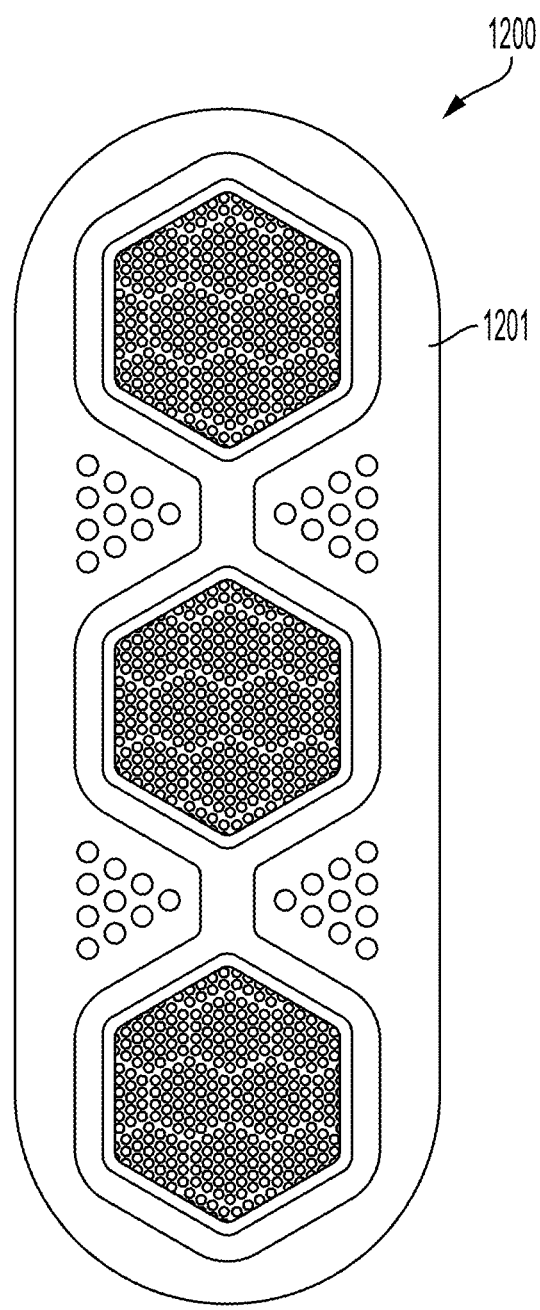
FIG. 12 is a top view of a second non-limiting exemplary membrane, in accordance with some embodiments.

In some embodiments, at least one of the first membrane implantation system and the second first membrane implantation system herein can comprise a membrane. A non-limiting first exemplary membrane 1100, per FIG. 11, can comprise a single membrane 1100 and a frame 1101 surrounding the membrane 1100. A non-limiting first exemplary membrane 1200, per FIG. 12, can comprise three membranes 1200 and a frame 1201 surrounding each membrane 1200.

In some embodiments, the membrane can comprise a cell. In some embodiments, the cells can be configured to produce insulin. In some embodiments, the membranes employed in the systems or by the devices herein can be held in a frame, wherein the frame can be rigid or semi-rigid. Further, in some embodiments, the frame can be a triplet frame configured to couple to, or contain, a plurality of membranes. Additional non-limiting exemplary membranes are shown in FIGS. 6, 7, 9, and 10.

Figure 13:
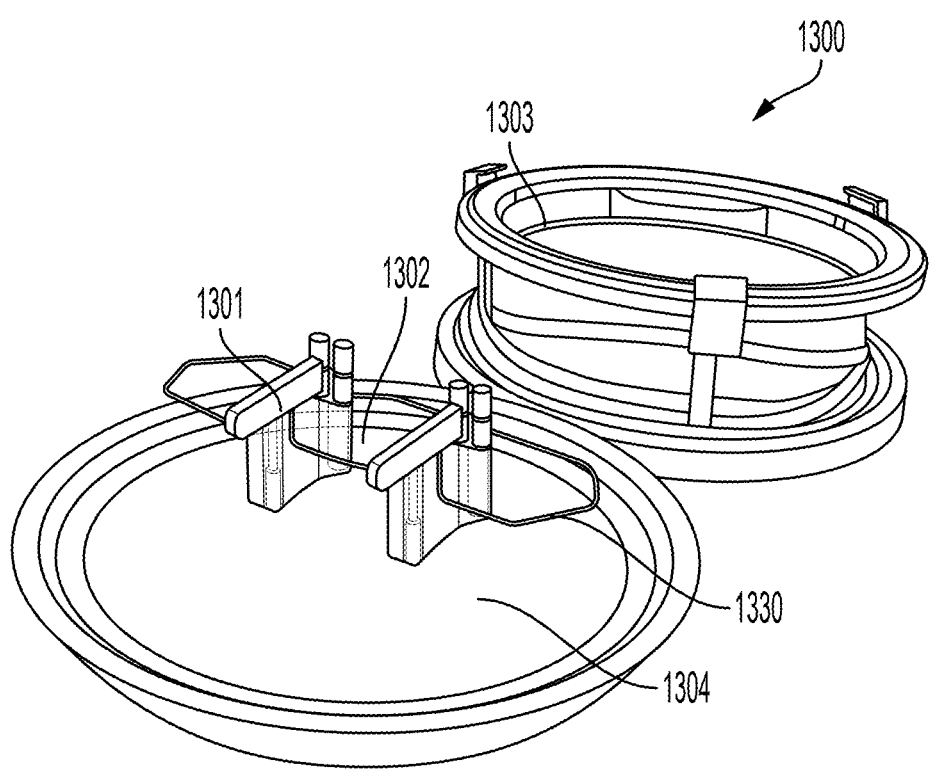
FIG. 13 is a top perspective view of a non-limiting exemplary membrane stand, in accordance with some embodiments.

In some embodiments per FIG. 13, the system can further comprise a membrane stand 1300 configured to temporarily affix the membrane 1330. In some embodiments, the membrane stand 1300 can be configured to temporarily affix the membrane 1330 during the insertion of the membrane 1330 into the first elongate body. Per FIG. 13, the membrane stand 1300 can comprise a clip 1301 configured to temporarily affix the membrane 1330 to the stand 1300. In some embodiments, the membrane stand 1300 can comprise a 1, 2, 3, or more clips 1301. In some embodiments, the membrane stand 1300 can comprises one less clips 1301 than the number of membranes 1330. In some embodiments, the clips 1301 can be configured to not contact the cell of the membrane 1330. In some embodiments, per FIG. 13, the membrane stand 1300 can further comprise a cover 1303 configured to cover the membrane on the stand 1300. In some embodiments, the cover 1303 can be further configured to seal the membrane 1330 within the membrane stand 1300. In some embodiments, per FIG. 13, the membrane stand 1300 can comprise a base 1304 connected to the clip 1301 and configured stabilize the clip 1301 on a surface. In some embodiments, per FIG. 13, the membrane stand 1300 can comprise a ledge 1302 attached to the base 1304 and configured to support a bottom side of the membrane 1330 against the clip 1301. In some embodiments, the membrane stand 1300 can comprise a 1, 2, 3, or more ledges 1302. In some embodiments, the membrane stand 1300 can comprise one less ledge 1302 than the number of membranes 1330. In some embodiments, the ledge 1301 can be configured to not contact the cell of the membrane 1330.

In some embodiments, at least one of the membrane stand 1300, the clip 1301, the ledge 1302, the cover 1303, and the base 1304 can be composed of metal, plastic, carbon fiber, fiberglass, wood, ceramic, or any combination thereof.

Figure 14:
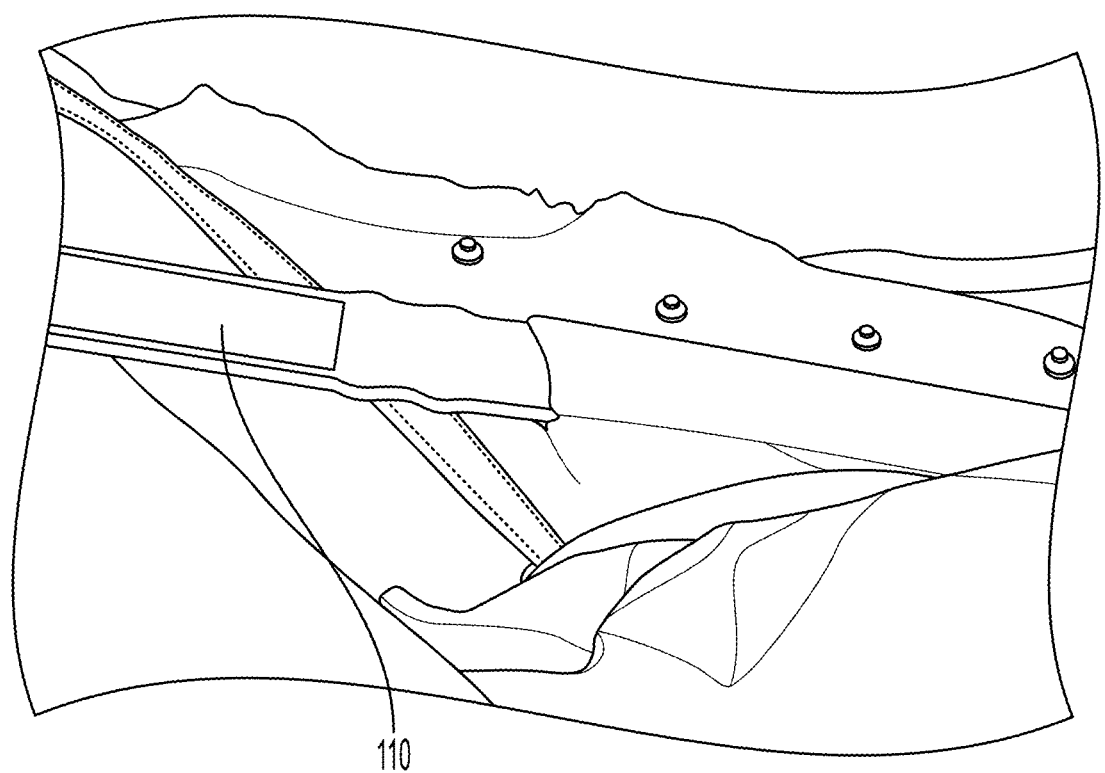
FIG. 14 is a first image of a non-limiting exemplary membrane implantation device subcutaneously implanting a membrane, in accordance with some embodiments.
Figure 15:
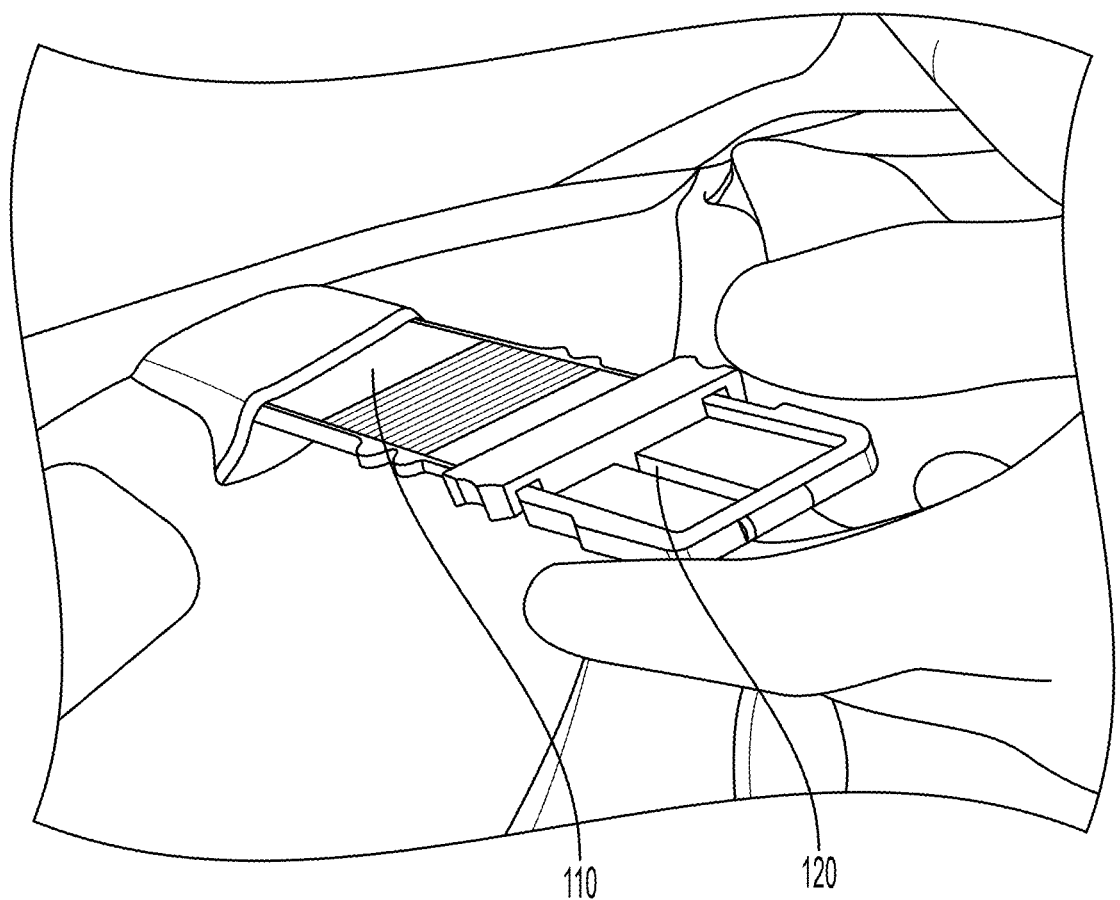
FIG. 15 is a second image of a non-limiting exemplary membrane implantation device subcutaneously implanting a membrane, in accordance with some embodiments.

Provided herein, for example, as shown in FIGS. 14 and 15, is an exemplary method for subcutaneously delivering a therapeutic comprising: directing the cells or therapeutics towards a delivery site and holding the cells or therapeutics at the delivery site, wherein the cells or therapeutics are held within an open volume of a first positioning body; withdrawing the first positioning body while the cells or therapeutics are held at the delivery site; and delivering the cells or therapeutics to the subject. In some embodiments, the method can be performed with the use of the membrane implantation device herein comprising a first elongate body 110 and a second elongate body 120.

In some embodiments, per FIGS. 6, 7, 9, and 10, the method can comprise placing a membrane 330 830 through a distal aperture or a proximal aperture of a membrane implantation device 300 800, subcutaneously inserting the distal portion of the first elongate body 310 810 into a subject; and translating the first elongate body 310 810 relative to the second elongate body 320 820 in a direction from the proximal aperture to the distal aperture, to remove the first elongate body 310 810 from the subject while maintaining the position of at least one of the membrane 330 830 and the second elongate body 320 820 with respect to the subject.

In some embodiments, the delivery site can be an implantation site for the cells or therapeutics. In some embodiments, the implantation site can comprise a subcutaneous or a pre-peritoneal implantation site. In some embodiments, directing the cells or therapeutics towards the delivery site can comprise directing the first positioning body towards the delivery site with the cells or therapeutics held within the open volume of the first positioning body. In some embodiments, directing the cells or therapeutics towards the delivery site, can comprise directing the cells or therapeutics to the open volume of the first positioning body via a delivery instrument. In some embodiments, withdrawing the first positioning body while the cells or therapeutics are held at the delivery site can further comprise preventing or obstructing movement of the cells or therapeutics with a second positioning body while withdrawing the first positioning body. In some embodiments, the second positioning body can be positioned within the open volume of the first positioning body. In some embodiments, withdrawing the first positioning body while the cells or therapeutics are held to the delivery site can comprise relative movement of the cells or therapeutics out of the first positioning body via an opening of the first positioning body. In some embodiments, the method can further comprise compressing the cells or therapeutics between tissue surfaces as the first positioning body is withdrawn. The method, in some embodiments, can allow delivery of the cells or therapeutics to the subject without the cells or therapeutics experiencing unprotected positive pressure. In some embodiments, the first positioning body can comprise titanium. In some embodiments, the cells or therapeutics can be held in a membrane. In some embodiments, the cells or therapeutics can be encapsulated in a membrane. In some embodiments, the cells can be insulin producing cells. In some embodiments, the membrane can be held in a frame. In some embodiments, the frame can be rigid or semi-rigid. In some embodiments, the frame can be a triplet frame configured to couple to a plurality of membranes.

In some embodiments, per FIG. 13, the method can further comprise placing the membrane 130 on a membrane stand 1300 before placing the membrane 1300 through the distal aperture or the proximal aperture of the first elongate body. In some embodiments, the method can further comprise compressing a clip 1301 against the membrane 1330. In some embodiments, the method can further comprise decompressing the clip 1301 from the membrane 1330 once the membrane 1330 is placed through the distal aperture or the proximal aperture of the first elongate body. In some embodiments, wherein the membrane stand 1300 can be configured to temporarily affix the membrane 1330 to insert the membrane 1330 into the first elongate body.

What is claimed is:

1. A device or system for delivering cells to a subject, the device or system comprising:
   a first elongate body comprising a proximal portion, a distal portion, and an open volume, wherein the open volume leads to an opening at the distal portion, wherein the opening comprises a dimension equal to or greater than about 1 cm;
   an encapsulation chamber disposed in the open volume, wherein the cells are disposed in the encapsulation chamber, wherein the encapsulation chamber includes a membrane configured to allow for diffusion of a therapeutic made by the cells; and
   a second elongate body comprising a proximal portion and a distal portion, wherein the distal portion of the second elongate body is sized to fit within the open volume of the first elongate body, and move relative to the first elongate body.

2. The device or system of claim 1, wherein the first elongate body is generally flat.

3. The device or system of claim 1, wherein the device or system comprises a volume equal to or less than about 40 cm3.

4. The device or system of claim 1, wherein a ratio of a width of the first elongate body to a height of the first elongate body is equal to or greater than about 5.

5. The device or system of claim 1 claims, wherein the first elongate body is comprised of titanium.

6. The device or system of claim 1, wherein the proximal portion of the first elongate body is proximal to the proximal portion of the second elongate body.

7. The device or system of claim 1, wherein the second elongate body comprises a cross sectional area generally equal to a cross sectional area of the open volume.

8. The device or system of claim 1, wherein the device or system has an average thickness equal to or less than about 1 cm.

9. The device or system of claim 1, wherein the device or system has an average thickness equal to or less than about 0.5 cm.

10. The device or system of claim 1, wherein the device or system has an average width equal to or less than about 5 cm.

11. The device or system of claim 1, wherein the first elongate body has a length equal to or less than about 30 cm.

12. The device or system of claim 1, wherein at least one of the first elongate body and the second elongate body have a normal cross-sectional shape comprising a circle, an oval, an ellipse, a triangle, a square, a regular polygon, an irregular polygon, or any combination thereof.

13. The device or system of claim 1, wherein at least one of the first elongate body and the second elongate body are generally straight in a direction from the proximal portion to the distal portion.

14. The device or system of claim 1, wherein centroids of cross sections of least one of the first elongate body and the second elongate body in a direction from the proximal portion to the distal portion form a line or a continuous curve, or both.

15. The device or system of claim 1, wherein the distal portion of the first elongate body comprises at least one of a fillet and a chamfer.

16. The device or system of claim 1, wherein the distal portion of the elongate body of the second elongate body comprises a divot along a width of the second elongate body.

17. The device or system of claim 16, wherein the divot is centered along the width of the second elongate body.

18. The device or system of claim 16, wherein the divot comprises a concave radius.

19. The device or system of claim 1, wherein at least one of the first elongate body and the second elongate body further comprises a stop, wherein the stop is configured to maintain the second elongate body within the open volume of the first elongate body.

20. The device or system of claim 1, wherein at least one of the first elongate body and the second elongate body further comprises a bearing.

21. The device or system of claim 1, wherein at least one of the first elongate body and the second elongate body are composed of metal, plastic, carbon fiber, fiberglass, wood, ceramic, or any combination thereof.

22. The device or system of claim 1, wherein at least one of the first elongate body and the second elongate body are composed of titanium, aluminum, stainless steel, or any combination thereof.

23. The device or system of claim 1, further comprising the therapeutic disposed in the encapsulation chamber.

24. The device or system of claim 1, wherein the therapeutic is insulin.

25. The device or system of claim 1, wherein the encapsulation chamber comprises a frame, and wherein a distal portion of the second elongate body conforms to a size and shape of the frame.

26. The device or system of claim 25, wherein the distal portion of the second elongate body comprises a surface with a concave curvature, and wherein the concave surface comprises a divot along a width of the second elongate body.

27. The device or system of claim 26, wherein the opening comprises a concave out curvature.

28. A method for delivering an encapsulation chamber containing cells to a subject, the method comprising:
   directing the encapsulation chamber containing the cells towards a delivery site;
   holding the encapsulation chamber containing the cells at the delivery site, wherein the encapsulation chamber is held within an open volume of a first positioning body;
   withdrawing the first positioning body while the encapsulation chamber is held at the delivery site; and
   delivering the encapsulation chamber containing the cells to the subject, wherein the encapsulation chamber includes a membrane configured to allow for diffusion of a therapeutic made by the cells.

29. The method of claim 28, further comprising the therapeutic disposed in the encapsulation chamber.

30. The method of claim 28, wherein the therapeutic is insulin.

31. The method of claim 28, wherein the encapsulation chamber comprises a frame, and wherein a distal portion of a second elongate body conforms to a size and shape of the frame.

32. The method of claim 31, wherein the distal portion of the second elongate body comprises a surface with a concave curvature, and wherein the concave surface comprises a divot along a width of the second elongate body.

33. The method of claim 32, wherein an opening of the first positioning body comprises a concave out curvature.

34. An encapsulation chamber implantation device comprising:
   a first elongate body comprising an elongated hollow body comprising an open volume having a distal aperture and a proximal aperture, wherein at least one of the open volume, the distal aperture and the proximal aperture;
   an encapsulation chamber disposed in the open volume;
   cells disposed in the encapsulation chamber, and wherein the encapsulation chamber includes a membrane configured to allow for diffusion of a therapeutic made by the cells; and
   a second elongate body configured to fit within the open volume of the first elongate body and to prevent translation of the encapsulation chamber in a direction from the distal aperture to the proximal aperture.

35. The device of claim 34, further comprising the therapeutic disposed in the encapsulation chamber.

36. The device of claim 34, wherein the therapeutic is insulin.

37. The device of claim 34, wherein the encapsulation chamber comprises a frame, and wherein a distal portion of the second elongate body conforms to a size and shape of the frame.

38. The device of claim 37, wherein the distal portion of the second elongate body comprises a surface with a concave curvature, and wherein the concave surface comprises a divot along a width of the second elongate body.

39. The device of claim 38, wherein the distal aperture comprises a concave out curvature.

40. A method for subcutaneously delivering cells comprising:
   placing an encapsulation chamber containing the cells through a distal aperture or a proximal aperture of an encapsulation chamber implantation device, the device comprising a second elongate body and a first elongate body comprising an elongated hollow body having an open volume;
   subcutaneously inserting a distal portion of the first elongate body into a subject; and
   translating the first elongate body relative to the second elongate body in a direction from the distal aperture to the proximal aperture, to remove the first elongate body from the subject while maintaining a position of at least one of the encapsulation chamber and the second elongate body with respect to the subject, wherein the encapsulation chamber includes a membrane configured to allow for diffusion of a therapeutic made by the cells.

41. The method of claim 40, further comprising the therapeutic disposed in the encapsulation chamber.

42. The method of claim 40, wherein the therapeutic is insulin.

43. The method of claim 40, wherein the encapsulation chamber comprises a frame, and wherein a distal portion of the second elongate body conforms to a size and shape of the frame.

44. The method of claim 43, wherein the distal portion of the second elongate body comprises a surface with a concave curvature, and wherein the concave surface comprises a divot along a width of the second elongate body.

45. The method of claim 44, wherein the distal aperture comprises a concave out curvature.

* * * * *

UNITED STATES PATENT AND TRADEMARK OFFICE
CERTIFICATE OF CORRECTION

| | | |
|---|---|---|
| PATENT NO. | : 12,377,252 B2 | Page 1 of 1 |
| APPLICATION NO. | : 16/980031 | |
| DATED | : August 5, 2025 | |
| INVENTOR(S) | : Christopher Thanos et al. | |

It is certified that error appears in the above-identified patent and that said Letters Patent is hereby corrected as shown below:

In the Claims

At Column 31, in Claim 3, on Line 40, please delete "cm3" and insert -- cm^3 --

Signed and Sealed this
Ninth Day of September, 2025

Coke Morgan Stewart
*Acting Director of the United States Patent and Trademark Office*